United States Patent
Engelhardt et al.

(10) Patent No.: US 8,258,129 B2
(45) Date of Patent: Sep. 4, 2012

(54) 4-HETEROCYCLOALKYLPYRI(MI)DINES, PROCESS FOR THE PREPARATION THEREOF AND THEIR USE AS MEDICAMENTS

(75) Inventors: Harald Engelhardt, Ebreichsdorf (AT); Gerd Bader, Vienna (AT); Guido Boehmelt, Gaaden (AT); Ralph Brueckner, Vienna (AT); Thomas Gerstberger, Vienna (AT); Maria Impagnatiello, Vienna (AT); Daniel Kuhn, Vienna (AT); Otmar Schaaf, Vienna (AT); Heinz Stadtmueller, Vienna (AT); Irene Waizenegger, Vienna (AT); Andreas Zoephel, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 574 days.

(21) Appl. No.: 12/304,134

(22) PCT Filed: Jul. 5, 2007

(86) PCT No.: PCT/EP2007/056853
§ 371 (c)(1),
(2), (4) Date: Feb. 24, 2009

(87) PCT Pub. No.: WO2008/003766
PCT Pub. Date: Jan. 10, 2008

(65) Prior Publication Data
US 2009/0203673 A1  Aug. 13, 2009

(30) Foreign Application Priority Data
Jul. 6, 2006  (EP) .................... 06116748

(51) Int. Cl.
*C07D 471/04* (2006.01)
*C07D 487/04* (2006.01)
*A61K 31/506* (2006.01)

(52) U.S. Cl. ............. 514/217.06; 514/227.8; 514/228.5; 514/230.5; 514/238.5; 514/249; 514/252.14; 514/252.18; 514/275; 540/600; 540/601; 544/60; 544/61; 544/122; 544/295; 544/323; 544/324

(58) Field of Classification Search .......... 540/600, 540/601; 544/60, 61, 122, 295, 323, 324; 514/217.06, 227.8, 228.5, 230.5, 238.5, 249, 514/252.14, 252.18, 275

See application file for complete search history.

(56) References Cited

U.S. PATENT DOCUMENTS

| | | | |
|---|---|---|---|
| 6,579,983 B1 * | 6/2003 | Batchelor et al. | 544/330 |
| 6,716,831 B1 * | 4/2004 | Breault et al. | 514/183 |
| 6,855,719 B1 * | 2/2005 | Thomas et al. | 514/269 |
| 2005/0256144 A1 * | 11/2005 | Kath et al. | 514/275 |
| 2006/0161001 A1 | 7/2006 | Hong et al. | |
| 2010/0093776 A1 * | 4/2010 | Beckwith | 514/275 |

FOREIGN PATENT DOCUMENTS

| | | | |
|---|---|---|---|
| CA | 2463989 A1 | | 4/2003 |
| WO | 03032997 A1 | | 4/2003 |
| WO | WO 03/030909 | * | 4/2003 |
| WO | WO 2004/089913 | * | 10/2004 |
| WO | WO 2006/038001 | * | 4/2006 |
| WO | 2006069258 A1 | | 6/2006 |

OTHER PUBLICATIONS

Byth et al., Imidzo[1,2-a]pyridines. Part 2: SAR and optimisation of a potent and selective class of cyclin-dependent kinase inhibitors, Bioorganic & Medicinal Chemistry Letters (2004), 14(9), pp. 2245-2248.*

Hughes et al., 4-aryl-5-cyano-2-aminopyrimidines as VEGF-R2 inhibitors: Synthesis and Biological evaluation, Bioorganic & Medicinal Chemistry Letters (Apr. 10, 2007), 17(12), pp. 3266-3270.*

International Search Report, Form PCT/ISA/210 for corresponding PCT/EP2007/056853, (2007).

* cited by examiner

*Primary Examiner* — Deepak Rao
(74) *Attorney, Agent, or Firm* — Michael P. Morris; Alan R. Stempel

(57) ABSTRACT

The present invention encompasses compounds of general formula (1)

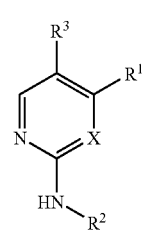

(1)

wherein X and $R^1$ to $R^3$ are as defined in the disclosure, which are suitable for the treatment of diseases characterized by excessive or abnormal cell proliferation, and the use thereof for preparing a pharmaceutical composition having the above-mentioned properties.

3 Claims, No Drawings

1

4-HETEROCYCLOALKYLPYRI(MI)DINES, PROCESS FOR THE PREPARATION THEREOF AND THEIR USE AS MEDICAMENTS

This application is a U.S. National Stage application of PCT/EP2007/056853 filed Jul. 5, 2007, which claims the benefit of EP06116748.2, filed on Jul. 6, 2006.

NEW COMPOUNDS

The present invention relates to new 4-heterocycloalkylpyrimidines of general formula (1)

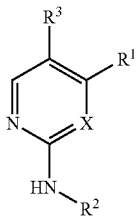

wherein the groups X and $R^1$ to $R^3$ have the meanings given in the claims and specification, the isomers thereof, processes for preparing these compounds and their use as medicaments.

DETAILED DESCRIPTION OF THE INVENTION

It has now surprisingly been found that compounds of general formula (1) wherein the groups X, $R^1$, $R^2$ and $R^3$ have the meanings given hereinafter act as inhibitors of specific cell cycle kinases. Thus, the compounds according to the invention may be used for example for the treatment of diseases connected with the activity of specific cell cycle kinases and characterised by excessive or abnormal cell proliferation.

The present invention relates to compounds of general formula (1)

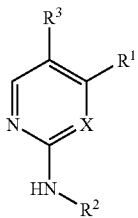

wherein
X denotes CH or N, and
$R^1$ denotes 8-12 membered heterocycloalkyl, optionally substituted by one or more identical or different $R^4$, and
$R^2$ denotes a group selected from among $C_{6-15}$aryl, 3-8 membered heterocycloalkyl and 5-14 membered heteroaryl, substituted by one or more identical or different $R^4$, and
$R^3$ denotes a group selected from among halogen, —CN, —$NR^fR^f$, —$OR^f$, —$C(O)R^f$, —$SR^f$, —$S(O)R^f$, —$S(O)_2R^f$, $C_{1-4}$alkyl, $C_{1-4}$haloalkyl, $C_{3-5}$cycloalkyl and 3-5 membered heterocycloalkyl, and
$R^4$ denotes a group selected from among $R^a$, $R^b$ and $R^a$ substituted by one or more identical or different $R^c$ and/or $R^b$;

each $R^a$ is selected independently of one another from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;
each $R^b$ is a suitable group and each is independently selected from among =O, —$OR^c$, $C_{1-3}$haloalkyloxy, —$OCF_3$, =S, —$SR^c$, =$NR^c$, =$NOR^c$, —$NR^cR^c$, halogen, —$CF_3$, —CN, —NC, —OCN, —SCN, —$NO_2$, —$S(O)R^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)_2NR^cR^c$, —$C(O)R^c$, —$C(O)OR^c$, —$C(O)NR^cR^c$, —$CN(R^f)NR^cR^c$, —$CN(OH)R^c$, —$CN(OH)NR^cR^c$, —$OC(O)R^c$, —$OC(O)OR^c$, —$OC(O)NR^cR^c$, —$OCN(R^f)NR^cR^c$, —$N(R^f)C(O)R^c$, —$N(R^f)C(S)R^c$, —$N(R^f)S(O)_2R^c$, —$N(R^f)C(O)OR^c$, —$N(R^f)C(O)NR^cR^c$, —[$N(R^f)C(O)]_2R^c$, —$N[C(O)]_2R^c$, —$N[C(O)]_2R^c$, —[$N(R^f)C(O)]_2OR^c$ and —$N(R^f)CN(R^f)NR^cR^c$;
each $R^c$ independently of one another denotes hydrogen or a group optionally substituted by one or more identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;
each $R^d$ independently of one another denotes hydrogen or a group optionally substituted by one or more identical or different $R^e$ and/or $R^f$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;
each $R^e$ is a suitable group and each is independently selected from among =O, —$OR^f$, $C_{1-3}$haloalkyloxy, —$OCF_3$, =S, —$SR^f$, =$NR^f$, =$NOR^f$, —$NR^fR^f$, halogen, —$CF_3$, —CN, —NC, —OCN, —SCN, —$NO_2$, —$S(O)R^f$, —$S(O)_2R^f$, —$S(O)_2OR^f$, —$S(O)NR^fR^f$, —$S(O)_2NR^fR^f$, —$OS(O)R^f$, —$OS(O)_2R^f$, —$OS(O)_2OR^f$, —$OS(O)_2NR^fR^f$, —$C(O)R^f$, —$C(O)OR^f$, —$C(O)NR^fR^f$, —$CN(R^g)NR^fR^f$, —$CN(OH)R^f$, —$C(NOH)NR^fR^f$, —$OC(O)R^f$, —$OC(O)OR^f$, —$OC(O)NR^fR^f$, —$OCN(R^g)NR^fR^f$, —$N(R^g)C(O)R^f$, —$N(R^g)C(S)R^f$, —$N(R^g)S(O)_2R^f$, —$N(R^d)C(O)OR^f$, —$N(R^g)C(O)NR^fR^f$, and —$N(R^g)CN(R^f)NR^fR^f$;
each $R^f$ independently of one another denotes hydrogen or a group optionally substituted by one or more identical or different $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;
each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkyl, 5-12 membered heteroaryl and 6-18 membered heteroarylalkyl, optionally in the form of the tautomers, the racemates, the enantiomers, the diastereomers and the mixtures thereof, and optionally the pharmacologically acceptable acid addition salts thereof, with the proviso that carries at least one substituent different from halogen and the following compounds are not included:
4-[5-chloro-4-(4,5,7,8-tetrahydro-1H-imidazo[4,5-d]azepin-6-yl)-pyrimidin-2-ylamino]-N,N-dimethyl-phenylsulphonamide, (2-99)
4-[5-chloro-4-(1,4,6,7-tetrahydro-imidazo[4,5-c]pyridin-5-yl)-pyrimidin-2-ylamino]-N,N-dimethyl-phenylsulphonamide (2-136)

N,N-dimethyl-4-[5-methyl-4-(1,4,6,7-tetrahydro-imidazo[4,5-c]pyridin-5-yl)-pyrimidin-2-ylamino]-phenylsulphonamide, (2-143)

N,N-dimethyl-4-[5-methyl-4-(4,5,7,8-tetrahydro-1H-imidazo[4,5-d]azepin-6-yl)-pyrimidin-2-ylamino]-phenylsulphonamide, (2-144)

2-(4-(1-piperidinyl-methyl-)phenylamino)-4-(1,4,6,7-tetrahydro-imidazo[4,5-c]pyridin-5-yl)-5-trifluoromethyl-pyrimidine; (1-006)

2-[4-(1,2,4,5-tetrahydro-benzo[d]azepin-3-ylmethyl)-phenylamino]-4-(1,4,6,7-tetrahydro-imidazo[4,5-c]pyridin-5-yl)-5-trifluoromethyl-pyrimidine; (1-646)

N,N-dimethyl-4-[4-(4,5,7,8-tetrahydro-1H-imidazo[4,5-d]azepin-6-yl)-5-trifluoromethyl-pyrimidin-2-ylamino]-phenylsulphonamide, (2-73)

N,N-dimethyl-4-[4-(3,4,6,7-tetrahydro-imidazo[4,5-c]pyridin-5-yl)-5-trifluoromethyl-pyrimidin-2-ylamino]-phenylsulphonamide, (1-694)

[4-(morpholin-4-sulphonyl)-phenyl]-[4-(3,4,6,7-tetrahydro-imidazo[4,5-c]pyridin-5-yl)-5-trifluoromethyl-pyrimidin-2-yl]-amine, (1-695)

[5-methoxy-4-(1,4,6,7-tetrahydro-imidazo[4,5-c]pyridin-5-yl)-pyrimidin-2-yl]-(4-piperidin-1-ylmethyl-phenyl)-amine, (2-139)

$N^5,N^5$-dimethyl-$N^2$-(4-piperidin-1-ylmethyl-phenyl)-4-(1,4,6,7-tetrahydro-imidazo[4,5-c]pyridin-5-yl)-pyrimidine-2,5-diamine, (2-145)

[5-isopropyl-4-(1,4,6,7-tetrahydro-imidazo[4,5-c]pyridin-5-yl)-pyrimidin-2-yl]-(4-piperidin-1-ylmethyl-phenyl)-amine, (2-146) 2-4-(carboxy-phenylamino)-4-(1,4,6,7-tetrahydro-imidazo[4,5-c]pyridin-5-yl)-5-trifluoromethyl-pyrimidine (1-017)

2-4-(2-carboxy-1-ethyl-)phenylamino)-4-(1,4,6,7-tetrahydro-imidazo[4,5-c]pyridin-5-yl)-5-trifluoromethyl-pyrimidine (1-023).

In one aspect the invention relates to compounds of general formula (1), wherein X denotes N.

In another aspect the invention relates to compounds of general formula (1), wherein $R^3$ denotes a group selected from among halogen, —$NR^fR^f$, —$OR^f$, —$C(O)R^f$, $C_{1-4}$alkyl, $C_{1-4}$haloalkyl and $C_{3-5}$cycloalkyl.

In another aspect the invention relates to compounds of general formula (1), wherein $R^2$ denotes a group selected from among phenyl and 5-12 membered heteroaryl.

In another aspect the invention relates to compounds of general formula (1A),

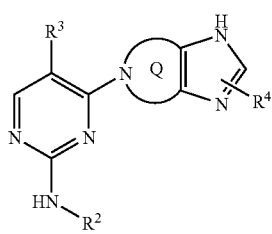

wherein
Q denotes 5, 6 or 7 membered heterocycloalkyl and
$R^2$, $R^3$ and $R^4$ are as hereinbefore defined.

(A) Aspects relating to $R^1$.

(A1) In one aspect the invention relates to compounds of general formula (1), wherein $R^1$ denotes 1,4,6,7-tetrahydro-imidazo[4,5-c]pyridin-5-yl.

(A2) In another aspect the invention relates to compounds of general formula (1), wherein $R^1$ denotes 4,5,7,8-tetrahydro-1H-imidazo[4,5-d]azepin-6-yl.

(B) Aspects relating to $R^2$.

(B1) In one aspect the invention relates to compounds of general formula (1), wherein $R^2$ denotes 9 membered heteroaryl, substituted by one or more identical or different $R^4$.

(B2) In another aspect the invention relates to compounds of general formula (1), wherein $R^2$ denotes 9 membered heterocycloalkyl substituted by one or more identical or different $R^4$.

(B3) In another aspect the invention relates to compounds of general formula (1), wherein $R^2$ denotes phenyl substituted by a 5-6 membered heterocycloalkyl, which may optionally be substituted by one or more identical or different $R^c$ and/or $R^b$.

(B4) In another aspect the invention relates to compounds of general formula (1), wherein $R^2$ denotes phenyl substituted by —$NR^cR^c$.

(B5) In another aspect the invention relates to compounds of general formula (1), wherein $R^2$ denotes phenyl substituted by —$C(O)R^c$.

(B6) In another aspect the invention relates to compounds of general formula (1), wherein $R^2$ denotes phenyl substituted by —$C(O)NR^cR^c$.

(C) Aspects relating to $R^3$.

(C1) In one aspect the invention relates to compounds of general formula (1), wherein $R^3$ denotes dimethylamino.

(C2) In another aspect the invention relates to compounds of general formula (1), wherein $R^3$ denotes methoxy.

All the above mentioned aspects (A1) and (A2) for $R^1$, (B1) to (B6) for $R^2$ and (C1) and (C2) for $R^3$ may be combined with one another as desired.

The following Table shows preferred combinations of different aspects of the compounds of formula I according to the invention:

| embodiment | $R^1$ | $R^2$ | $R^3$ |
|---|---|---|---|
| I-1 | A1 | B1 | C1 |
| I-2 | A1 | B2 | C1 |
| I-3 | A1 | B3 | C1 |
| I-4 | A1 | B4 | C1 |
| I-5 | A1 | B5 | C1 |
| I-6 | A1 | B6 | C1 |
| I-7 | A2 | B1 | C1 |
| I-8 | A2 | B2 | C1 |
| I-9 | A2 | B3 | C1 |
| I-10 | A2 | B4 | C1 |
| I-11 | A2 | B5 | C1 |
| I-12 | A2 | B6 | C1 |
| I-13 | A1 | B1 | C2 |
| I-14 | A1 | B2 | C2 |
| I-15 | A1 | B3 | C2 |
| I-16 | A1 | B4 | C2 |
| I-17 | A1 | B5 | C2 |
| I-18 | A1 | B6 | C2 |
| I-19 | A2 | B1 | C2 |
| I-20 | A2 | B2 | C2 |
| I-21 | A2 | B3 | C2 |
| I-22 | A2 | B4 | C2 |
| I-23 | A2 | B5 | C2 |
| I-24 | A2 | B6 | C2 |

In another aspect the invention relates to compounds of general formula (1) or (1A), or the pharmaceutically effective salts thereof, for use as pharmaceutical compositions.

In another aspect the invention relates to compounds of general formula (1) or (1A), or the pharmaceutically effective salts thereof, for preparing a pharmaceutical composition with an antiproliferative activity.

In another aspect the invention relates to pharmaceutical preparations containing as active substance one or more compounds of general formula (1) or (1A), or the pharmaceutically effective salts thereof optionally in combination with conventional excipients and/or carriers.

In another aspect the invention relates to the use of compounds of general formula (1) or (1A) for preparing a pharmaceutical composition for the treatment and/or prevention of cancer, infections, inflammations and autoimmune diseases.

In another aspect the invention relates to a pharmaceutical preparation comprising a compound of general formula (1) or (1A) and at least one other antiproliferative active substance, different from formula (1) or (1A), optionally in the form of the tautomers, the racemates, the enantiomers, the diastereomers and the mixtures thereof, and optionally the pharmaceutically effective salts thereof.

DEFINITIONS

As used herein, the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

Heteroalkyl represents unbranched or branched aliphatic hydrocarbon chains which contain 1 to 3 heteroatoms, while each of the available carbon and heteroatoms in the heteroalkyl chain may optionally each be substituted independently and the heteroatoms independently of one another are selected from among O, N, P, PO, $PO_2$, S, SO and $SO_2$ (e.g. dimethylaminomethyl, dimethylaminoethyl, dimethylaminopropyl, diethylaminomethyl, diethylaminoethyl, diethylaminopropyl, 2-diisopropylaminoethyl, bis-2-methoxyethylamino, [2-(dimethylamino-ethyl)-ethyl-amino]-methyl, 3-[2-(dimethylamino-ethyl)-ethyl-amino]-propyl, hydroxymethyl, 2-hydroxyethyl, 3-hydroxypropyl, methoxy, ethoxy, propoxy, methoxymethyl, 2-methoxyethyl).

Haloalkyl refers to alkyl groups wherein one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF=CF_2$, —$CCl=CH_2$, —$CBr=CH_2$, —$CI=CH_2$, —$C≡C-CF_3$, —$CHFCH_2CH_3$ and —$CHFCH_2CF_3$.

Halogen refers to fluorine, chlorine, bromine and/or iodine atoms.

By cycloalkyl is meant a mono- or polycyclic ring, wherein the ring system may be a saturated ring but also an unsaturated, non-aromatic ring or a spiro compound, which may optionally also contain double bonds, such as for example cyclopropyl, cyclopropenyl, cyclobutyl, cyclobutenyl, cyclopentyl, cyclopentenyl, cyclohexyl, cyclohexenyl, cycloheptanyl, cycloheptenyl, norbornyl, norbornenyl, indanyl, adamantyl, spiroheptanyl and spiro[4.2]heptanyl.

Cycloalkylalkyl includes a non-cyclic alkyl as hereinbefore defined wherein a hydrogen atom bound to a carbon atom is replaced by a cycloalkyl group.

Aryl relates to monocyclic or bicyclic rings with 6-12 carbon atoms such as for example phenyl and naphthyl.

Arylalkyl includes a non-cyclic alkyl group wherein a hydrogen atom bound to a carbon atom is replaced by an aryl group.

By heteroaryl are meant mono- or polycyclic rings which contain, instead of one or more carbon atoms, one or more heteroatoms, which may be identical or different, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridinyl, imidazopyridinyl, naphthyridinyl, indolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl wherein a hydrogen atom bound to a carbon atom is replaced by a heteroaryl group.

Heterocycloalkyl relates to saturated or unsaturated, non-aromatic mono-, polycyclic or bridged polycyclic rings or spiro compounds comprising 3-12 carbon atoms, which carry heteroatoms, such as nitrogen, oxygen or sulphur, instead of one or more carbon atoms. Examples of such heterocyclyl groups are tetrahydrofuranyl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2,2,1]heptane, 3,8-diaza-bicyclo[3.2.1]octane, 3,9-diaza-bicyclo[4.2.1]nonane and 2,6-diaza-bicyclo[3.2.2]nonane.

Heterocycloalkylalkyl relates to a non-cyclic alkyl group wherein a hydrogen atom bound to a carbon atom is replaced by a heterocycloalkyl group.

By the word "substituted" is meant that a hydrogen atom which is bound directly to the atom in question is replaced by a different atom or a different atomic group. Bivalent substituents such as =O, =S, =NR, =NOR, =NNRR, =NN(R)C(O)NRR, =N$_2$ and others demand substitution by two hydrogen atoms which are bound directly to the atom in question. Accordingly, bivalent substituents of this kind may not be substituents in aromatic systems.

| List of abbreviations | | | |
|---|---|---|---|
| DMA | N,N-dimethylacetamide | min | minute(s) |
| DMF | N,N-dimethylformamide | MS | mass spectrometry |
| DMSO | dimethylsulphoxide | RP | Reversed phase |
| Et | ethyl | RT | room temperature |
| h | hour(s) | sec | second(s) |
| HPLC | high performance liquid chromatography | THF | tetrahydrofuran |
| Me | methyl | UV | ultraviolet |

PREPARATION OF THE COMPOUNDS ACCORDING TO THE INVENTION

The compounds according to the invention may be prepared according to the methods of synthesis described hereinafter, wherein the substituents of general formulae (I to XIV) have the meanings given hereinbefore.

Method

Step 1

The preparation of the intermediate compound III is carried out by substitution of a leaving group (LG), for example halogen, SCN or methoxy, preferably chlorine, in a heteroaromatic system I by a nucleophile II.

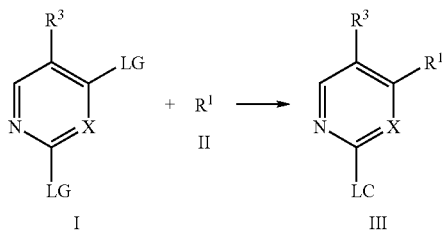

Scheme 1

1 equivalent of compound I and 1-1.5 equivalents of compound II are stirred in a solvent, for example 1,4-dioxane, THF, DMF, DMA or 2-butanol. At a temperature of 15-25° C. 2-2.5 equivalents of a base, for example potassium carbonate, sodium carbonate, caesium carbonate, ethyldiisopropylamine or triethylamine, are added. The reaction mixture is stirred for a further 12-72 h at a temperature of 15-50° C. Then the solvent is distilled off and the residue is purified by chromatography.

Step 2

The preparation of the end compound V is carried out by substitution of a leaving group LG, for example halogen, SCN or methoxy, preferably chlorine, in a heteroaromatic system III by a nucleophile IV.

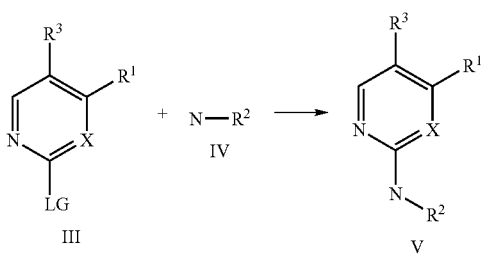

Scheme 2

1 equivalent of the compound III and 1-3 equivalents of the compound IV are stirred in a solvent, for example 1,4-dioxane, DMF, DMA, N-methyl-2-pyrrolidinone or water. At a temperature of 15-40° C. 1-2 equivalents of an inorganic acid, for example sulphuric acid or hydrochloric acid, are added. The reaction mixture is stirred for a further 12-72 h at a temperature of 20-100° C. Then the solvent is distilled off and the residue is purified by chromatography.

Step 3A

For groups R$^2$ which contain, in addition to the N atom mentioned above, another N atom, a carbonyl group, a halogen atom or another functional group, there is the possibility of further derivatisation to obtain the product VIII. For example it is possible to react molecules which have a further N atom with a reactant having a carbonyl group (VII).

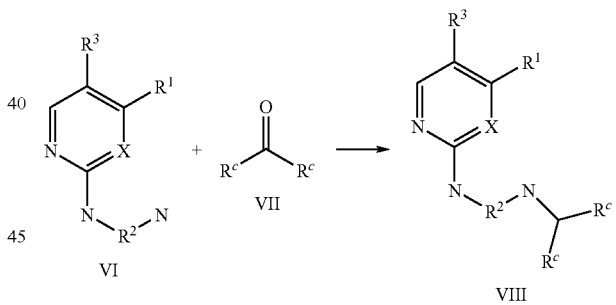

Scheme 3A 1 equivalent of the compound VI and 1-2 equivalents of the compound VII are stirred in a solvent, for example methanol or DMA. At a temperature of 15-25° C., 2-5 equivalents of a reducing agent, for example sodium triacetoxyborohydride or sodium cyanoborohydride, are added. The reaction mixture is stirred for a further 0.5-18 h at a temperature of 15-25° C., then combined with water, which has been adjusted to a pH of 8 to 9 with an inorganic base, for example sodium hydrogen carbonate, potassium carbonate or sodium hydroxide. This mixture is extracted two to three times with an organic solvent, for example diethyl ether, ethyl acetate or dichloromethane. The combined organic extracts are dried and the solvent is distilled off. The residue is purified by chromatography or repeated crystallisation.

Step 3B

In addition, molecules with a carbonyl group may be reacted with an amine.

Scheme 3B

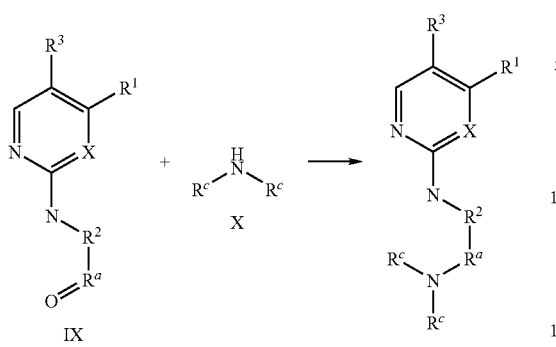

1 equivalent of the compound IX and 1-2 equivalents of the compound X are stirred in a solvent, for example methanol or DMA. At a temperature of 15-25° C., 2-5 equivalents of a reducing agent, for example sodium triacetoxyborohydride or sodium cyanoborohydride, are added. The reaction mixture is stirred for a further 0.5-18 h at a temperature of 15-25° C., then combined with water, which has been adjusted to a pH of 8 to 9 with an inorganic base, for example sodium hydrogen carbonate, potassium carbonate or sodium hydroxide. This mixture is extracted two to three times with an organic solvent, for example diethyl ether, ethyl acetate or dichloromethane. The combined organic extracts are dried and the solvent is distilled off. The residue is purified by chromatography or repeated crystallisation.

Step 3C

Molecules with an additional N atom may be reacted with an alkyl halide (alkyl-Hal).

Scheme 3C

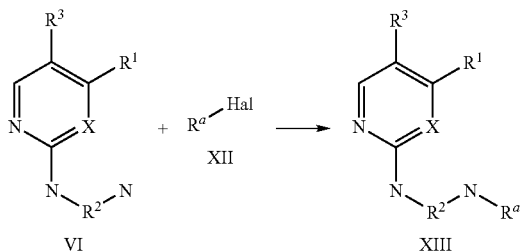

1 equivalent of the compound VI and 1-10 equivalents of the compound XII are stirred in a solvent, for example 1,4-dioxane, THF, DMF or acetonitrile. At a temperature of 15-25° C., 2-2.5 equivalents of a base, for example potassium carbonate, sodium carbonate, caesium carbonate, ethyldiisopropylamine or triethylamine, are added. The reaction mixture is stirred for a further 12-72 h at a temperature of 15-25° C., then combined with water, which has been adjusted to a pH of 8-9 with an inorganic base, for example sodium hydrogen carbonate or potassium carbonate. This mixture is extracted two to three times with an organic solvent, for example diethyl ether, ethyl acetate or dichloromethane. The combined organic extracts are dried and the solvent is distilled off. The residue is purified by chromatography or repeated crystallisation.

Step 3D

Molecules that have a carboxyl group may be reacted with an amine. If the carboxyl group is present in a protected form it is converted into the deprotected compound beforehand by hydrolysis or similar methods known to the skilled man.

Scheme 3D

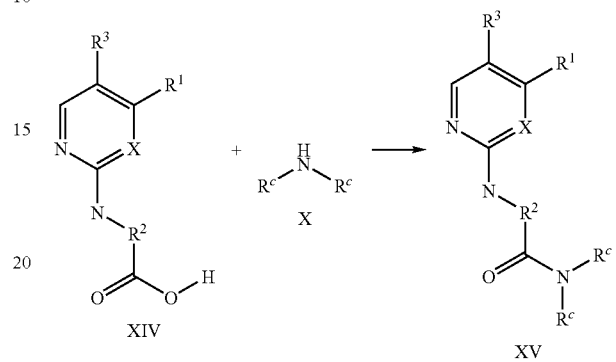

1 equivalent of the compound XIV, 1-1.5 equivalents of the compound X and 1-3 equivalents of a base, for example triethylamine or ethyldiisopropylamine, are stirred in a solvent, for example 1,4-dioxane, DMF, DMA or N-methyl-2-pyrrolidinone. At a temperature of 15-25° C., 1-1.5 equivalents of a coupling reagent, for example N,N-dicyclohexylcarbodiimide, N,N-diisopropylcarbodiimide, O-(benzotriazol-1-yl)-N,N,N',N'-tetramethyluronium-tetrafluoroborate, 1-(3-N,N-dimethylaminopropyl)-3-ethylcarbodiimide or O-(7-azabenzotriazol-1-yl)-N,N,N',N'-tetramethyluronium hexafluorophosphate, are added. The reaction mixture is stirred for a further 4-24 h at a temperature of 15-25° C. Then the solvent is distilled off and the residue is purified by chromatography.

Chromatography

For the preparative medium pressure chromatography (MPLC) silica gel obtained from Millipore (Granula Silica Si-60A 35-70 µm) or C-18 RP silica gel obtained from Macherey Nagel (Polygoprep 100-50 C18) is used.

For the high pressure chromatography, columns made by Waters (XTerra Prep. MS C18, 5 µM, 30*100 mm, Symmetrie C18, 5 µm, 19*100 mm or XBridge C18, 5 µm, 19*100) are used.

Mass Spectroscopy/UV-Spectrometer:

These data are produced using an HPLC-MS apparatus (high performance liquid chromatography with mass detector) made by Agilent.

The apparatus is constructed so that the chromatography (column: Zorbax SB-C8, 3.5 µm, 2.1*50, Agilent) is followed by a diode array detector (G1315B made by Agilent) and a mass detector (1100 LS-MSD SL; G1946D; Agilent) connected in series.

This apparatus is operated with a flow of 0.6 mL/min. For a separation process a gradient is run through within 3.5 min (gradient at the start: 95% water and 5% acetonitrile, gradient at the finish: 5% water and 95% acetonitrile; as buffer, either 0.1% formic acid is added to both solvents, or 5 mM ammonium hydrogen carbonate and 19 mM ammonia are added to the water).

Starting Materials

Where the preparation of the starting compounds has not been described, these are commercially obtainable, known from the literature or are easily obtained by the skilled man using general methods.

- (2,4-dichloro-pyrimidin-5-yl)-dimethyl-amine and derivatives (O'Brien, Darrell E. et al., J. Med. Chem. (1966), 9, 121)
- 4,5,6,7-tetrahydro-1H-imidazo[4,5-c]pyridine (T. Vitali et al., Farmacao, Ed. Sci. 20, 636 (1969))
- 1-methyl-4,5,6,7-tetrahydro-1H-imidazo[4,5-c]pyridine (R. Jain, L. A. Cohen, Tetrahedron, 52 (15) 5363 (1996) or T. Vitali et al., Farmacao, Ed. Sci. 20, 636 (1969))
- 3-methyl-4,5,6,7-tetrahydro-1H-imidazo[4,5-c]pyridine (G. Durant et. al, J. Med. Chem. (1976), 19, 923 or T. Vitali et al., Farmacao, Ed. Sci. 20, 636 (1969))
- 4,5,6,7-tetrahydro-1H-imidazo[4,5-d]-azepine (WO 03/032997)
- 2-methyl-4,5,6,7-tetrahydro-1H-imidazo[4,5-d]-azepine (WO 03/032997)
- 2-thiomethyl-4,5,6,7-tetrahydro-1H-imidazo[4,5-d]-azepine (analogously to 2-methyl-4,5,6,7-tetrahydro-1H-imidazo[4,5-d]-azepine with S-methylthiourea)
- N-(3-aminophenyl)pyrrolidine-1-carboxamide (WO 2004/048343)
- 4-morpholin-4-yl-cyclohexylamine and 4-morpholin-4-yl-cyclobutylamine (WO 2006/021544)
- 2-thiomethyl-4,5,6,7-tetrahydro-1H-imidazo[4,5-d]-azepine (analogously to 2-methyl-4,5,6,7-tetrahydro-1H-imidazol[4,5-d]-azepine with S-methylthiourea)
- Aminobenzylamines are commercially obtainable, may be prepared analogously to Monatsh. Chem. (1969), 100(4) or by corresponding methods known to the skilled man.
- Aminobenzimidazoles are commercially obtainable, may be prepared analogously to Olguín, Luís F.; Synlett (2005), (2), 340-342, Bapat; Shirsat, Indian J. Chem.; 3; 1965; 81, Ainsworth, D. P.; Suschitzky, H. J. Chem. Soc., Org. (1966), (1), 111-13 or by corresponding methods known to the skilled man.
- 4-aminoanilines are commercially obtainable, may be prepared analogously to WO 2006/021548 or by corresponding methods known to the skilled man.
- 1-methyl-4-piperazin-1-yl-1H-pyridin-2-one may be obtained for example by methylation of 4-benzyloxy-1H-pyridin-2-one and subsequent debenzylation (Gwaltney, S. L. et al, Bioorganic & Medicinal Chemistry Letters (2001), 11(7), 871-874) and reaction with Bocpiperazine (in toluene, 120° C., water separator) with subsequent deprotection or by similar methods known to the skilled man.

Method 1

4-methyl-4,5,6,7-tetrahydro-1H-imidazo[4,5-c]pyridine

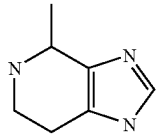

1.5 g Histamine (×2HCl) are dissolved in 100 mL phosphate buffer (pH 7) and combined with 1.6 mL acetaldehyde. The pH of the reaction solution is adjusted to 8 by the addition of 1 N NaOH and the reaction solution is stirred for 5 days at 37° C. Then the pH is adjusted to 12 by the further addition of 1 N NaOH, the solvent is eliminated in vacuo, the residue is suspended in ethanol and filtered to remove any undissolved constituents. After elimination of the ethanol in vacuo a crude product remains, which is further used directly for the following reactions.

Yield: 1.62 g
MS: 138 (M+H)$^+$ 4-ethyl-4,5,6,7-tetrahydro-1H-imidazo[4,5-c]pyridine is prepared analogously to 4-methyl-4,5,6,7-tetrahydro-1H-imidazo[4,5-c]pyridine using 2.2 mL propionaldehyde.

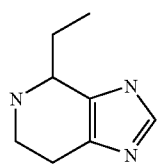

Yield: 1.8 g
MS: 152 (M+H)$^+$

Method 2

(R)-6-methyl-4,5,6,7-tetrahydro-1H-imidazo[4,5-c]pyridine

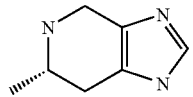

a) (S)-1-bromomethyl-2-(3H-imidazol-4-yl)-ethylamine 900 mg (S)-histidinol (×2HCl) are dissolved in 20 mL HBr in acetic acid (32%) and heated to 110° C. in the microwave for 6 h. The solvent is eliminated in vacuo, the residue is dissolved in ethanol and again freed from the solvent in vacuo. This crude product is used in the next reaction step without further purification.

Yield: 1.5 g
MS: 204/206 (M+H)$^+$ b) (R)-2-(3H-imidazol-4-yl)-1-methyl-ethylamine 1.5 g (S)-1-bromomethyl-2-(3H-imidazol-4-yl)-ethylamine and 1.87 g sodium acetate are dissolved in 94 mL acetic acid (10%). After the addition of 400 mg palladium/C the suspension is shaken under 3.5 bar H$_2$ pressure at RT for about 60 h. After the catalyst has been filtered off the solvent is eliminated in vacuo and the crude product is used without further purification in the following reaction step.

c) (R)-6-methyl-4,5,6,7-tetrahydro-1H-imidazo[4,5-c]pyridine 0.5 g (R)-2-(3H-imidazol-4-yl)-1-methyl-ethylamine are dissolved in 50 mL phosphate buffer (pH 7) and combined with 1.35 mL formaldehyde. The pH is adjusted to 8 by the addition of 1 N NaOH and the reaction solution is stirred for 12 h at 37° C. Then by the further addition of 1 N NaOH the pH is adjusted to 12, the solvent is eliminated in vacuo, the residue is suspended in ethanol and filtered to remove any undissolved constituents. After elimination of the ethanol in vacuo a crude product is left which is further used directly for the following reactions.

(S)-6-methyl-4,5,6,7-tetrahydro-1H-imidazo[4,5-c]pyridine is prepared analogously to (R)-6-methyl-4,5,6,7-tetrahydro-1H-imidazo[4,5-c]pyridine using 900 mg (R)-histidinol (×2HCl).

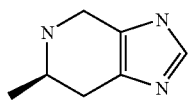

Method 3

7-methyl-3a.4,5,6,7.7a-hexahydro-1H-imidazo[4,5-c]pyridine

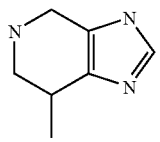

a) (1-trityl-1H-imidazol-4-yl)-acetonitrile 2.5 g (1H-imidazol-4-yl)-acetonitrile are dissolved in 20 mL DMF. After the addition of 3.6 mL triethylamine and 7.25 g chlorotriphenylmethane the suspension is left for 60 h at RT with stirring. Water and ethyl acetate are added, the organic phase is separated off, dried with $MgSO_4$ and the solvent is eliminated in vacuo.
Yield: 8.15 g
MS: 243 ($CPh_3^+$)

b) 2-(1-trityl-1H-imidazol-4-yl)-propionitrile 9.2 g (1-trityl-1H-imidazol-4-yl)-acetonitrile are dissolved in 120 mL THF, the solution is cooled to −5° C. and 1.8 mL methyl iodide and 1.08 g sodium hydride (60%) are added. The suspension is stirred for 12 h at RT and then applied directly to RP gel and purified by RP chromatography (C18, 10/90 to 90/10 acetonitrile/water in 15 min-0.2% formic acid is added to both solvents).
Yield: 3.23 g
MS: 243 ($CPh_3^+$)

c) 2-(1-trityl-1H-imidazol-4-yl)-propylamine 3.2 g 2-(1-trityl-1H-imidazol-4-yl)-propionitrile are dissolved in 150 mL methanolic ammonia (7 mol/L) and Raney nickel is added. After 12 h and 4 bar $H_2$ pressure the catalyst is filtered off and the solvent is eliminated in vacuo. This crude product is used in the following reaction step without further purification.
Yield: 3.2 g
MS: 243 ($CPh_3^+$)

d) 7-methyl-3a.4,5,6,7.7a-hexahydro-1H-imidazo[4, 5-c]pyridine 3.2 g 2-(1-trityl-1H-imidazol-4-yl)-propylamine is suspended in aqueous HCl (1 N). After the addition of 2.9 mL formaldehyde the mixture is heated to 95° C. with stirring. After 5 h it is cooled to RT, suction filtered to remove the precipitate formed and the solvent is eliminated in vacuo. This crude product is used in the following reaction step without further purification.
Yield: 2.47 g
MS: 138 (M+H)$^+$ Example 1

2-(4-piperazin-1-yl-phenylamino)-4-(3,4,6,7-tetrahydro-imidazo[4,5-c]pyridin-5-yl)-5-methoxy-pyrimidine

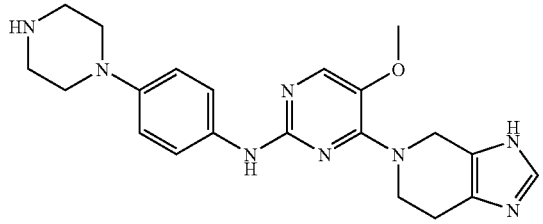

a) benzyl 4-(4-nitro-phenyl)-piperazine-1-carboxylate 3.76 mL 4-fluoronitrobenzene are dissolved in 40 mL DMA and combined with 9.25 mL N-ethyldiisopropylamine and 7.6 mL 1-(benzyloxycarbonyl)-piperazine. The reaction mixture is stirred for 18 h at 80° C. Then the solvent is eliminated in vacuo and the crude product is purified by chromatography. The carrier material used is silica gel and the eluant is a mixture consisting of cyclohexane/ethyl acetate (50/50).
Yield: 11.28 g
MS (ESI): 342 (M+H)$^+$ b) benzyl 4-(4-amino-phenyl)-piperazine-1-carboxylate 11.28 g benzyl 4-(4-nitro-phenyl)-piperazine-1-carboxylate are dissolved in 500 mL MeOH and combined with 1 g Raney nickel. The mixture is hydrogenated for 18 h at 5 bar $H_2$ pressure. Then the mixture is filtered to remove the catalyst, 70 mL of 1 N aqueous hydrochloric acid are added and the solvent is eliminated in vacuo.
Yield: 10.89 g
MS (ESI): 312 (M+H)$^+$ c) 2-chloro-4-(3,4,6,7-tetrahydro-imidazo[4,5-c] pyridin-5-yl)-5-methoxy-pyrimidine 1 g 2,4-dichloro-5-methoxy-pyrimidine are dissolved in 4 mL butanol and combined with 1.04 g 4,5,6,7-tetrahydroimidazopyridine dihydrochloride and 2.96 mL ethyldiisopropylamine. This mixture is stirred for 16 h at 50° C. and then the solvent is eliminated in vacuo. The crude mixture is purified by column chromatography. The carrier material used is C18-

RP-silica gel and a gradient is run through which consists at the starting point of 95% water and 5% acetonitrile and at the finishing point of 70% water and 30% acetonitrile. 0.2% formic acid is added to both eluants. The suitable fractions are freeze-dried.

Yield: 0.47 g
MS (ESI): 266 (M+H)$^+$ d) 2-(4-piperazin-1-yl-phenylamino)-4-(3,4,6,7-tetrahydro-imidazo[4,5-c]pyridin-5-yl)-5-methoxy-pyrimidine 100 mg 2-chloro-4-(3,4,6,7-tetrahydro-imidazo[4,5-c]pyridin-5-yl)-5-methoxy-pyrimidine are suspended in 0.26 mL 1,4-dioxane and 40 µL water and combined with 196 mg benzyl 4-(4-amino-phenyl)-piperazine-1-carboxylate hydrochloride (prepared according to Method 4). This mixture is heated to 95° C. and stirred for 20 h at this temperature. The suspension obtained is diluted with DMF and then purified by column chromatography. The carrier material used is C18-RP-silica gel and a gradient is run through which consists at the starting point of 95% water and 5% acetonitrile and at the finishing point of 70% water and 30% acetonitrile. 0.2% formic acid is added to both eluants. The suitable fractions are freeze-dried. 140 mg of the intermediate product thus obtained are combined with 15 mL DMF, 8 mL water and 30 mg palladium hydroxide and hydrogenated for 2 h at 7 bar H$_2$ pressure. The catalyst is filtered off and the solvent is eliminated in vacuo.

Yield: 0.47 g
UV max: 282 nM
MS (ESI): 407 (M+H)$^+$

Example 2-52

The following compounds are prepared by a process analogous to that described in Example 1. The preparation of 2-chloro-4-(3,4,6,7-tetrahydro-imidazo[4,5-c]pyridin-5-yl)-5-dimethylamino-pyrimidine is described in Example 63.

| # | R$^2$ | MS (ESI) (M + H)$^+$ | UV max [nm] |
|---|---|---|---|
| 2 | X$_2$–phenyl–N(piperazine)–C(O)–N(morpholine) | 533 | 290 |
| 3 | X$_2$–phenyl–N(piperidine)–OH | 435 | 290 |
| 4 | X$_2$–phenyl–N(piperazine)–N(pyridine) | 497 | 266/286 |
| 5 | X$_2$–phenyl–N(piperazine)–N(pyrimidine) | 498 | 246/290 |
| 6 | X$_2$–phenyl–N(piperazine)–CH$_2$–C(O)–N(morpholine) | 547 | 290 |
| 7 | cyclohexyl–N(CH$_3$)–phenyl–X$_2$ | 447 | 285 |

-continued
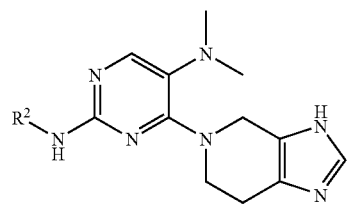
| # | R² | MS (ESI) (M + H)⁺ | UV max [nm] |
|---|---|---|---|
| 8 | X₂—⟨phenyl⟩—N(piperazine)N—CH₂—C(O)—NH—iPr | 519 | 290 |
| 9 | X₂—⟨phenyl⟩—N(bicyclic)—N—CH₃ | 446 | 294 |
| 10 | X₂—⟨phenyl⟩—N(piperazine)N—S(O)₂—Et | 512 | 290 |
| 11 | X₂—⟨phenyl⟩—N(piperazine)N—C(O)CH₃ | 462 | 290 |
| 12 | X₂—⟨phenyl⟩—N(piperidine)—C(O)—⟨3,5-dichloro-4-aminophenyl⟩ | 607 | 298 |
| 13 | X₂—⟨phenyl⟩—N(piperidine)—C(O)—⟨4-fluorophenyl⟩ | 541 | 290 |
| 14 | X₂—⟨phenyl⟩—N(piperidine)—C(O)OCH₃ | 477 | 290 |
| 15 | X₂—⟨phenyl⟩—N(oxabicyclic) | 433 | 294 |
| 16 | X₂—⟨phenyl⟩—N(pyrrolidine)—CH₂OCH₃ | 449 | 294 |

-continued
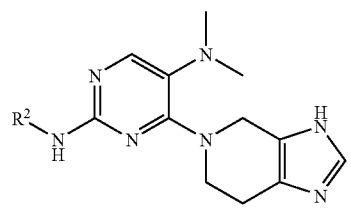
| # | R² | MS (ESI) (M + H)⁺ | UV max [nm] |
|---|---|---|---|
| 17 | 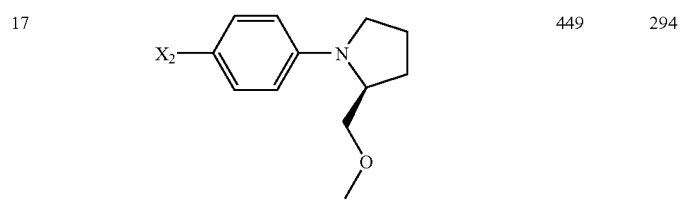 | 449 | 294 |
| 18 | 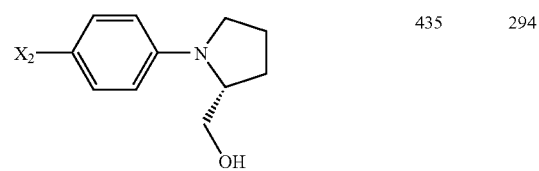 | 435 | 294 |
| 19 | 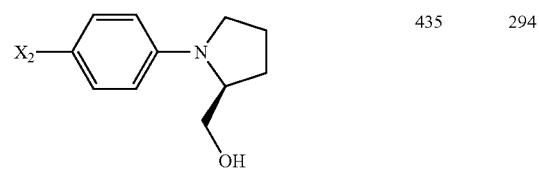 | 435 | 294 |
| 20 | 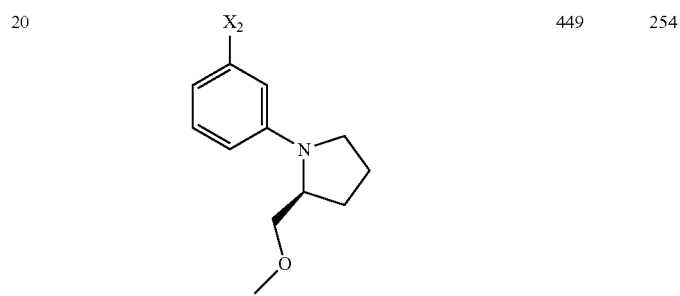 | 449 | 254 |
| 21 | 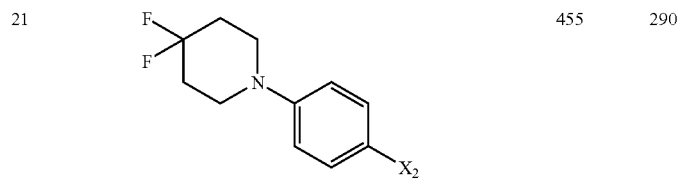 | 455 | 290 |
| 22 | 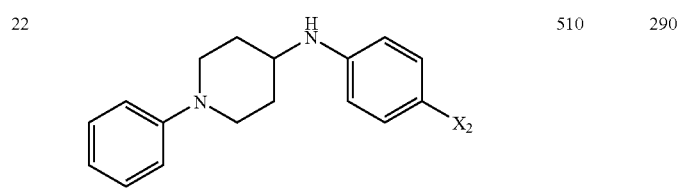 | 510 | 290 |

-continued
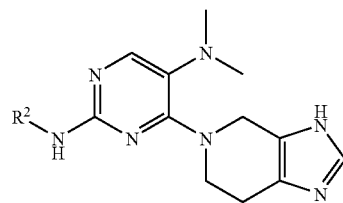
| # | R² | MS (ESI) (M + H)⁺ | UV max [nm] |
|---|---|---|---|
| 23 | 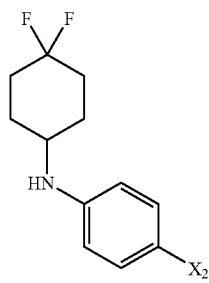 | 469 | 290 |
| 24 | 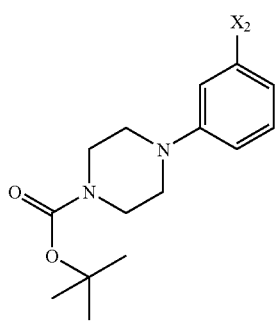 | 520 | 246 |
| 25 | 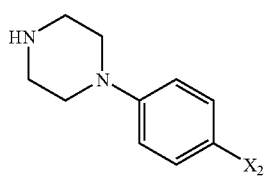 | 420 | 290 |
| 26 | 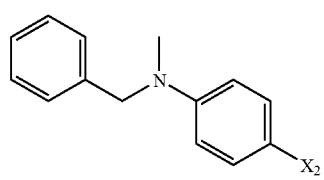 | 455 | 295 |
| 27 | 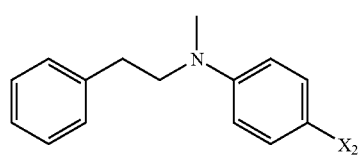 | 469 | 295 |
| 28 | 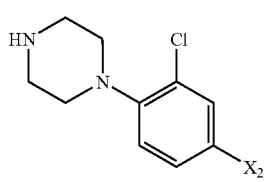 | 454 | 290 |

-continued
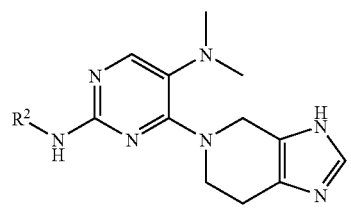
| # | R² | MS (ESI) (M + H)⁺ | UV max [nm] |
|---|---|---|---|
| 29 | 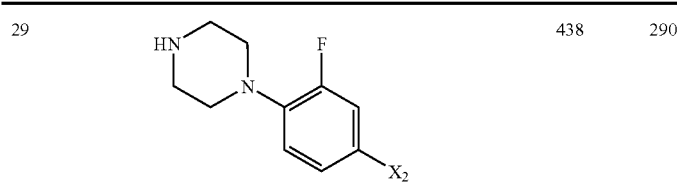 | 438 | 290 |
| 30 | 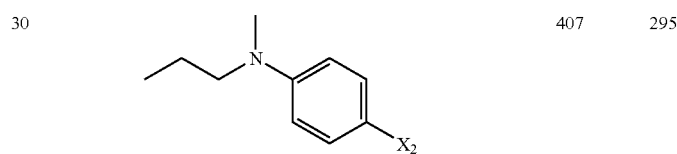 | 407 | 295 |
| 31 | 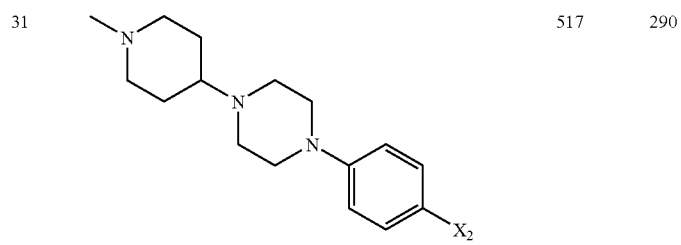 | 517 | 290 |
| 32 | 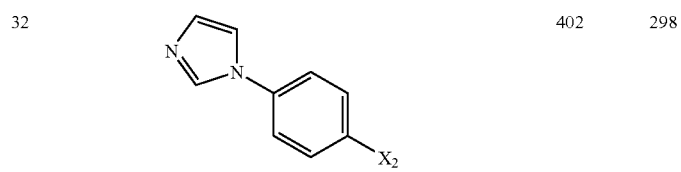 | 402 | 298 |
| 33 | 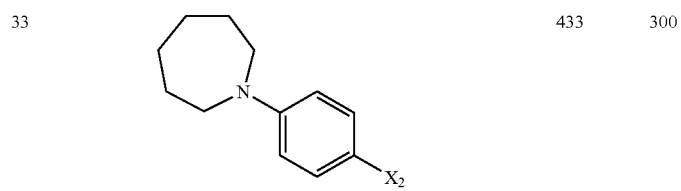 | 433 | 300 |
| 34 | 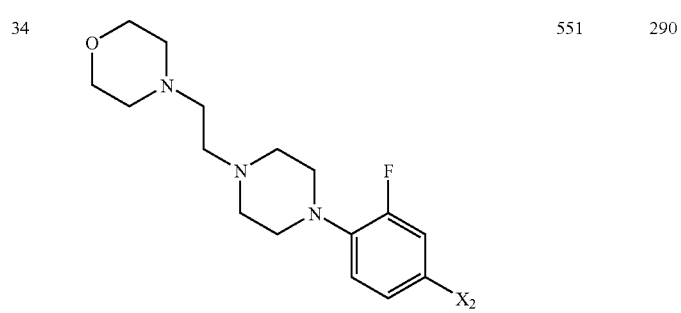 | 551 | 290 |

-continued
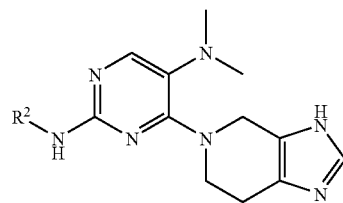
| # | R² | MS (ESI) (M + H)⁺ | UV max [nm] |
|---|---|---|---|
| 35 | | 535 | 290 |
| 36 | | 462 | 294 |
| 37 | | 435 | 290 |
| 38 | | 502 | 290 |
| 39 | | 565 | 294 |
| 40 | | 434 | 290 |

-continued
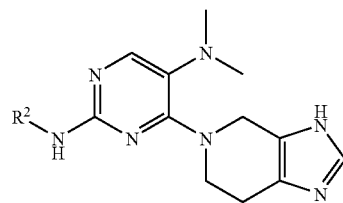
| # | R² | MS (ESI) (M + H)⁺ | UV max [nm] |
|---|---|---|---|
| 41 | 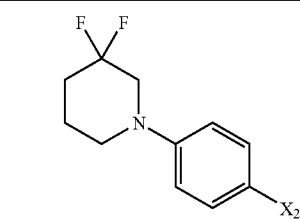 | 455 | 290 |
| 42 | 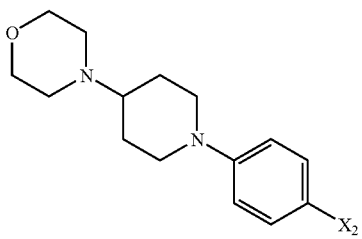 | 504 | 290 |
| 43 | 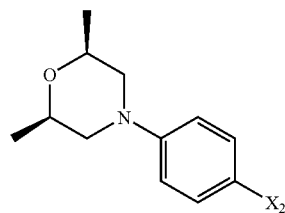 | 449 | 290 |
| 44 | 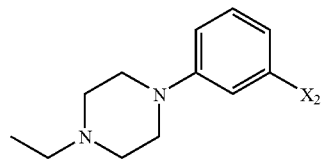 | 448 | 246, 286 |
| 45 | 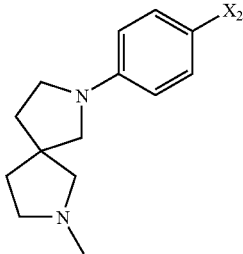 | 474 | 294 |
| 46 | 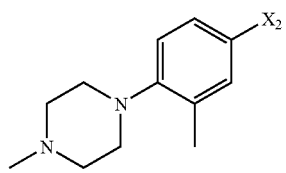 | 448 | 290 |

-continued
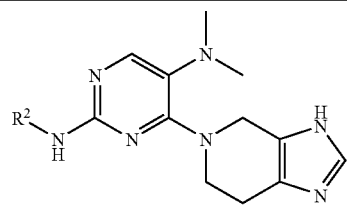
| # | R² | MS (ESI) (M + H)⁺ | UV max [nm] |
|---|---|---|---|
| 47 | (3-pyridyloxy-phenyl)-X₂ | 429 | 286 |
| 48 | (4-methylpiperazinyl, 2-methoxy-phenyl)-X₂ | 464 | 294 |
| 49 | (4-methylimino-pyridinyl-phenyl)-X₂ | 422 | 322 |
| 50 | (tetrahydropyran-4-yloxy-phenyl)-X₂ | 436 | 286 |
| 51 | (thiomorpholine-S-oxide-phenyl)-X₂ | 453 | 290 |
| 52 | (thiomorpholine-S,S-dioxide-phenyl)-X₂ | 469 | 294 |

Example 53

2-[4-(4-isopropyl)-(piperazin-1-yl-phenylamino)-4-(3,4,6,7-tetrahydro-imidazo[4,5-c]pyridin-5-yl)-5-methoxy-pyrimidine

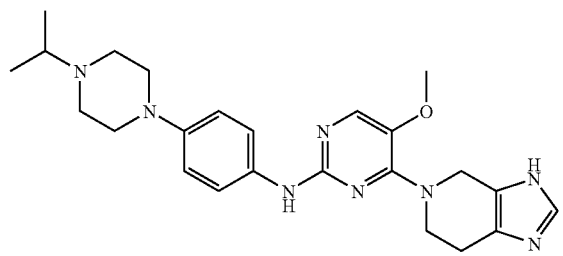

30 mg 2-(4-piperazin-1-yl-phenylamino)-4-(3,4,6,7-tetrahydro-imidazo[4,5-c]pyridin-5-yl)-5-methoxy-pyrimidine (see Example 1) are dissolved in 0.2 mL DMF. After the addition of 2 µL glacial acetic acid, 11 µL acetone and 78 mg sodium triacetoxyborohydride the suspension is stirred for 3 h at RT. After the addition of 100 µL water the reaction solution is purified by chromatography. The carrier material used is C18-RP-silica gel and a gradient is run through which consists at the starting point of 85% water and 15% acetonitrile and at the finishing point of 5% water and 95% acetonitrile. 0.2% $NH_3/KHCO_3$ is added to both eluants. The suitable fractions are freeze-dried.

Yield: 22 mg
UV max: 282 nM
MS (ESI): 449 (M+H)$^+$

Example 54-62

The following compounds are prepared by a process analogous to that described in Example 53. The preparation of 2-chloro-4-(3,4,6,7-tetrahydro-imidazo[4,5-c]pyridin-5-yl)-5-dimethylamino-pyrimidine is described in Example 63.

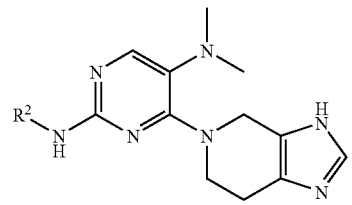

| # | R$^2$ | MS (ESI) (M + H)$^+$ | UV max [nm] |
|---|---|---|---|
| 54 | | 460 | 290 |
| 55 | 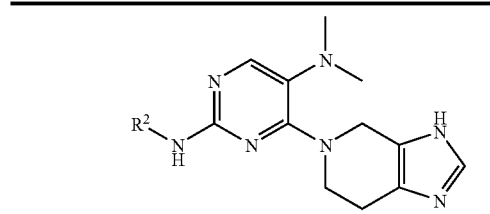 | 532 | 290 |
| 56 | 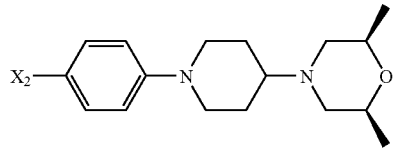 | 532 | 286 |
| 57 | 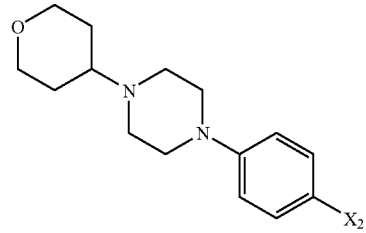 | 504 | 290 |
| 58 | 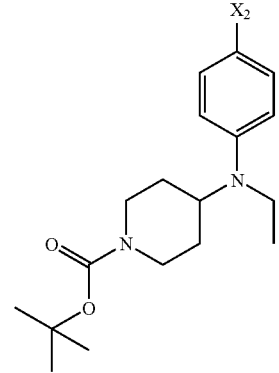 | 562 | 278 |
| 59 | 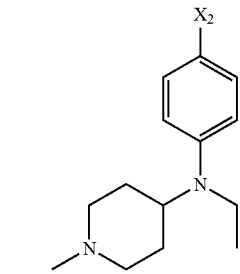 | 476 | 294 |
| 60 | 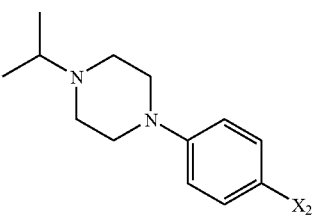 | 462 | 290 |

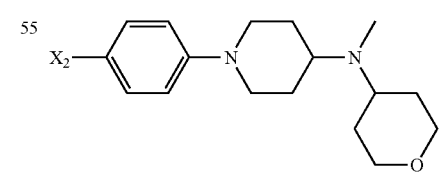

-continued

| # | R² | MS (ESI) (M + H)⁺ | UV max [nm] |
|---|---|---|---|
| 61 | 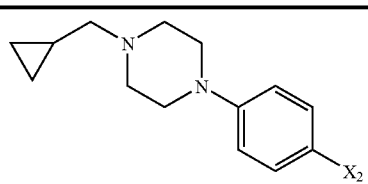 | 474 | 290 |
| 62 | 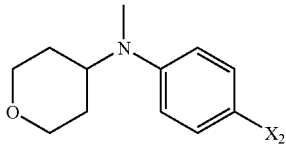 | 449 | 294 |

Example 63

2-(4-dimethylaminomethyl-phenylamino)-4-(3,4,6,7-tetrahydro-imidazo[4,5-c]pyridin-5-yl)-5-dimethylamino-1-pyrimidine

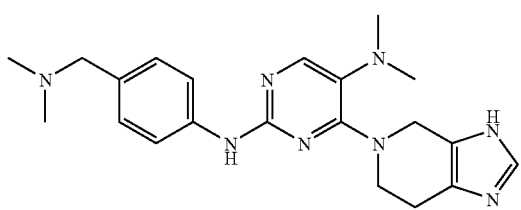

a) 2-chloro-4-(3,4,6,7-tetrahydro-imidazo[4,5-c]pyridin-5-yl)-5-dimethylamino-pyrimidine 5 g of 2,4-dichloro-5-dimethylamino-pyrimidine are dissolved in 30 mL isopropanol and combined with 5.82 g 4,5,6,7-tetrahydroimidazopyridine dihydrochloride and 6.06 g potassium carbonate. After 6 and 8 days in each case 1 g of 4,5,6,7-tetrahydroimidazopyridine dihydrochloride and 1 g potassium carbonate are added. In all, the mixture is stirred for 10 days at 25° C. The reaction mixture is diluted with 400 mL water and stirred for 1 h. The precipitate formed is suction filtered, washed and dried.

Yield: 6.24 g

MS (ESI): 279 (M+H)⁺ b) 2-(4-dimethylaminomethyl-phenylamino)-4-(3,4,6,7-tetrahydro-imidazo[4,5-c]pyridin-5-yl)-5-dimethylamino-pyrimidine 50 mg 2-chloro-4-(3,4,6,7-tetrahydro-imidazo[4,5-c]pyridin-5-yl)-5-dimethylamino-pyrimidine are suspended in 60 µL of 1,4-dioxane, 20 µL water and 90 µL of a 5 M hydrochloric acid (in 1,4-dioxane) and mixed with 55 mg 4-dimethylaminomethyl-phenylamine. This mixture is heated to 95° C. and stirred for 20 h at this temperature. The suspension obtained is diluted with DMF and then purified by column chromatography. The carrier material used is C18-RP-silica gel and a gradient is run through which consists at the starting point of 95% water (10 mM ammonium hydrogen carbonate and 38 mM ammonia) and 5% acetonitrile and at the finishing point of 50% water and 50% acetonitrile. The fractions are freeze-dried. The residue is taken up in acetonitrile, combined with aqueous hydrochloric acid and freeze-dried once more.

Yield: 8 mg

UV max: 290 nM

MS (ESI): 393 (M+H)⁺

Example 64-191

The following compounds are prepared by a process analogous to that described in Example 63.

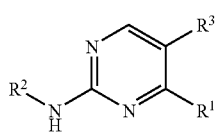

| # | R¹ | R² | R³ | MS (ESI) (M + H)⁺ | UV max [nm] |
|---|---|---|---|---|---|
| 64 | 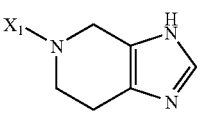 | 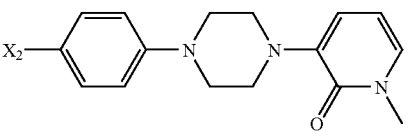 | —NMe₂ | 527 | 290 |

-continued

| # | R¹ | R² | R³ | MS (ESI) (M + H)⁺ | UV max [nm] |
|---|---|---|---|---|---|
| 65 | X₁–[tetrahydroimidazopyridine] | 2-(thiophen-2-yl)-1H-benzimidazol-5-yl (X₂) | —NMe₂ | 458 | 270; 346 |
| 66 | X₁–[tetrahydroimidazopyridine] | 4-(1H-pyrazol-1-yl)phenyl (X₂) | —NMe₂ | 402 | 302-306 |
| 68 | X₁–[tetrahydroimidazopyridine] | 2-(methylthio)benzothiazol-6-yl (X₂) | —NMe₂ | 439 | 230; 326 |
| 69 | X₁–[tetrahydroimidazopyridine] | 2-methylbenzothiazol-5-yl (X₂) | —NMe₂ | 407 | 242; 290 |
| 70 | X₁–[tetrahydroimidazopyridine] | N-propyl-3-fluoro-4-(X₂)benzamide | —NMe₂ | 439 | 314 |
| 71 | X₁–[tetrahydroimidazopyridine] | 2-(trifluoromethyl)-1H-benzimidazol-5-yl (X₂) | —NMe₂ | 444 | 234; 254; 318 |
| 72 | X₁–[tetrahydroimidazopyridine] | 2-methylbenzoxazol-5-yl (X₂) | —NMe₂ | 391 | 230 |

-continued

| # | R¹ | R² | R³ | MS (ESI) (M + H)⁺ | UV max [nm] |
|---|---|---|---|---|---|
| 73 | 4,5,6,7-tetrahydroimidazo[4,5-c]pyridin-5-yl (X₁) | 2-oxo-2,3-dihydrobenzo[d]oxazol-6-yl (X₂) | —NMe₂ | 393 | 286 |
| 74 | 4,5,6,7-tetrahydroimidazo[4,5-c]pyridin-5-yl (X₁) | 2-methylbenzo[d]oxazol-6-yl (X₂) | —NMe₂ | 391 | 218; 310 |
| 77 | 4,5,6,7-tetrahydroimidazo[4,5-c]pyridin-5-yl (X₁) | 1-methyl-1H-indol-5-yl (X₂) | —NMe₂ | 389 | 274 |
| 78 | 4,5,6,7-tetrahydroimidazo[4,5-c]pyridin-5-yl (X₁) | 3-(methylsulfonamido)phenyl (X₂) | —NMe₂ | 429 | 218-222; 286 |
| 79 | 4,5,6,7-tetrahydroimidazo[4,5-c]pyridin-5-yl (X₁) | 3-(dimethylamino)phenyl (X₂) | —NMe₂ | 379 | 250 |
| 80 | 4,5,6,7-tetrahydroimidazo[4,5-c]pyridin-5-yl (X₁) | 1-acetyl-2,3-dihydro-1H-indol-6-yl (X₂) | —NMe₂ | 419 | 246; 258 |
| 81 | 4,5,6,7-tetrahydroimidazo[4,5-c]pyridin-5-yl (X₁) | 3-acetamidophenyl (X₂) | —NMe₂ | 393 | 238 |
| 82 | 4,5,6,7-tetrahydroimidazo[4,5-c]pyridin-5-yl (X₁) | 2-oxoindolin-6-yl (X₂) | —NMe₂ | 391 | 238 |

-continued

| # | R¹ | R² | R³ | MS (ESI) (M + H)⁺ | UV max [nm] |
|---|---|---|---|---|---|
| 83 | 4,5,6,7-tetrahydroimidazo[4,5-c]pyridin-5-yl (X₁-N) | 2-propyl-6-X₂-isoindolin-1-one | —NMe₂ | 433 | 222-234; 286-290 |
| 84 | 4,5,6,7-tetrahydroimidazo[4,5-c]pyridin-5-yl (X₁-N) | 2,2-dimethyl-6-X₂-2H-benzo[b][1,4]oxazin-3(4H)-one | —NMe₂ | 435 | 234-238 |
| 85 | 4,5,6,7-tetrahydroimidazo[4,5-c]pyridin-5-yl (X₁-N) | 7-X₂-2H-benzo[b][1,4]oxazin-3(4H)-one | —NMe₂ | 407 | 306 |
| 86 | 4,5,6,7-tetrahydroimidazo[4,5-c]pyridin-5-yl (X₁-N) | 4-X₂-N,N-dimethylbenzylamine | —NMe₂ | 393 | 290 |
| 87 | 4,5,6,7-tetrahydroimidazo[4,5-c]pyridin-5-yl (X₁-N) | 2-ethyl-5-X₂-1H-benzimidazole | —NMe₂ | 404 | 230, 282, 310 |
| 88 | 4,5,6,7-tetrahydroimidazo[4,5-c]pyridin-5-yl (X₁-N) | 4-X₂-N,N-dimethylaniline | —NMe₂ | 379 | 294 |
| 89 | 4,5,6,7-tetrahydroimidazo[4,5-c]pyridin-5-yl (X₁-N) | 4-X₂-N-ethyl-N-methylbenzylamine | —NMe₂ | 407 | 285 |
| 90 | 4,5,6,7-tetrahydroimidazo[4,5-c]pyridin-5-yl (X₁-N) | 1-(4-X₂-benzyl)-1H-imidazole | —NMe₂ | 416 | 260, 285 |

-continued

| # | R¹ | R² | R³ | MS (ESI) (M + H)⁺ | UV max [nm] |
|---|---|---|---|---|---|
| 91 | 4,5,6,7-tetrahydro-imidazo[4,5-c]pyridin-5-yl (X₁-N) | 4-(X₂)benzyl-2,5-dihydro-pyrrol-1-yl | —NMe₂ | 417 | 285 |
| 92 | 4,5,6,7-tetrahydro-imidazo[4,5-c]pyridin-5-yl (X₁-N) | N-butyl-N-methyl-(4-X₂-benzyl)amino | —NMe₂ | 435 | 285 |
| 93 | 4,5,6,7-tetrahydro-imidazo[4,5-c]pyridin-5-yl (X₁-N) | 3,5-dimethyl-1-(4-X₂-benzyl)piperidin-1-yl | —NMe₂ | 461 | 290 |
| 94 | 4,5,6,7-tetrahydro-imidazo[4,5-c]pyridin-5-yl (X₁-N) | 4-methoxy-1-(4-X₂-benzyl)piperidin-1-yl | —NMe₂ | 463 | 285 |
| 95 | 4,5,6,7-tetrahydro-imidazo[4,5-c]pyridin-5-yl (X₁-N) | 4-(trifluoromethyl)-1-(4-X₂-benzyl)piperidin-1-yl | —NMe₂ | 501 | 282 |

-continued

| # | R¹ | R² | R³ | MS (ESI) (M + H)⁺ | UV max [nm] |
|---|---|---|---|---|---|
| 96 | 4,5,6,7-tetrahydroimidazo[4,5-c]pyridin-5-yl (X₁-N) | N-cyclopentyl-N-methyl-(4-X₂-benzyl)amine | —NMe₂ | 447 | 290 |
| 97 | 4,5,6,7-tetrahydroimidazo[4,5-c]pyridin-5-yl (X₁-N) | N-cyclohexyl-N-methyl-(4-X₂-benzyl)amine | —NMe₂ | 461 | 290 |
| 98 | 4,5,6,7-tetrahydroimidazo[4,5-c]pyridin-5-yl (X₁-N) | 4-X₂-acetanilide | —NMe₂ | 393 | 295 |
| 99 | 4,5,6,7-tetrahydroimidazo[4,5-c]pyridin-5-yl (X₁-N) | 1-(4-X₂-phenyl)piperidine | —NMe₂ | 419 | 290 |
| 100 | 4,5,6,7-tetrahydroimidazo[4,5-c]pyridin-5-yl (X₁-N) | N-phenyl-4-X₂-aniline | —NMe₂ | 427 | 305 |
| 101 | 4,5,6,7-tetrahydroimidazo[4,5-c]pyridin-5-yl (X₁-N) | 1-(1-methylpiperidin-4-yl)-4-(4-X₂-phenyl)piperazine | —NMe₂ | 517 | 290 |
| 103 | 4,5,6,7-tetrahydroimidazo[4,5-c]pyridin-5-yl (X₁-N) | 1-[2-(4-X₂-phenyl)ethyl]piperidine | —NMe₂ | 447 | 286 |

-continued
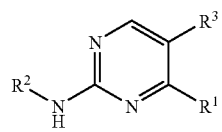
| # | R¹ | R² | R³ | MS (ESI) (M + H)⁺ | UV max [nm] |
|---|---|---|---|---|---|
| 104 | | | —NMe₂ | 461 | 258, 282 |
| 106 | | | —NMe₂ | 390 | 250, 326 |
| 107 | | | —NMe₂ | 392 | 282, 306 |
| 108 | | | —NMe₂ | 442 | 266, 342 |
| 109 | | | —NMe₂ | 447 | 250, 290 |
| 110 | | | —NMe₂ | 391 | 286 |
| 111 | | | —NMe₂ | 463/465 | 290 |
| 112 | | | —NMe₂ | 420 | 290 |

-continued

| # | R¹ | R² | R³ | MS (ESI) (M + H)⁺ | UV max [nm] |
|---|---|---|---|---|---|
| 113 | 4,5,6,7-tetrahydroimidazo[4,5-c]pyridin-5-yl (X₁-) | 4-(4-methylpiperazin-1-yl)-3-fluorophenyl (-X₂) | —NMe₂ | 452 | 290 |
| 114 | 4,5,6,7-tetrahydroimidazo[4,5-c]pyridin-5-yl (X₁-) | 4-(4-ethylpiperazin-1-yl)phenyl (-X₂) | —NMe₂ | 448 | 290 |
| 115 | 4,5,6,7-tetrahydroimidazo[4,5-c]pyridin-5-yl (X₁-) | 3-(pyrrolidine-1-carboxamido)phenyl (-X₂) | —NMe₂ | 448 | 282 |
| 116 | 4,5,6,7-tetrahydroimidazo[4,5-c]pyridin-5-yl (X₁-) | 4-fluorophenyl (-X₂) | —NMe₂ | 354 | 278 |
| 117 | 4,5,6,7-tetrahydroimidazo[4,5-c]pyridin-5-yl (X₁-) | 2-oxoindolin-5-yl (-X₂) | —NMe₂ | 391 | 290 |
| 118 | 4,5,6,7-tetrahydroimidazo[4,5-c]pyridin-5-yl (X₁-) | 1-(methylsulfonyl)indolin-5-yl (-X₂) | —NMe₂ | 455 | 290 |
| 119 | 4,5,6,7-tetrahydroimidazo[4,5-c]pyridin-5-yl (X₁-) | 5-(4-methylpiperazin-1-yl)pyridin-2-yl (-X₂) | —NMe₂ | 435 | 290 |
| 121 | 4,5,6,7-tetrahydroimidazo[4,5-c]pyridin-5-yl (X₁-) | 1-methyl-1H-benzo[d]imidazol-5-yl (-X₂) | —NMe₂ | 390 | 242, 278, 314 |

-continued

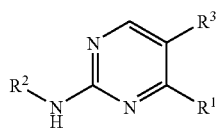

| # | R¹ | R² | R³ | MS (ESI) (M + H)⁺ | UV max [nm] |
|---|---|---|---|---|---|
| 122 | (4,5,6,7-tetrahydro-3H-imidazo[4,5-c]pyridin-5-yl, X₁) | (1,2-dimethyl-1H-benzimidazol-5-yl, X₂) | —NMe₂ | 404 | 238, 282 |
| 123 | (4,5,6,7-tetrahydro-3H-imidazo[4,5-c]pyridin-5-yl, X₁) | (1-methyl-2-oxo-2,3-dihydro-1H-benzimidazol-5-yl, X₂) | —NMe₂ | 406 | 286 |
| 124 | (4,5,6,7-tetrahydro-3H-imidazo[4,5-c]pyridin-5-yl, X₁) | (1-(2-hydroxyethyl)-1H-benzimidazol-5-yl, X₂) | —NMe₂ | 420 | 238, 278, 314 |
| 125 | (4,5,6,7-tetrahydro-3H-imidazo[4,5-c]pyridin-5-yl, X₁) | (1-(2-hydroxyethyl)-2-methyl-1H-benzimidazol-5-yl, X₂) | —NMe₂ | 434 | 238, 282, 314 |
| 126 | (4,5,6,7-tetrahydro-3H-imidazo[4,5-c]pyridin-5-yl, X₁) | (1-(2-hydroxyethyl)-2-ethyl-1H-benzimidazol-5-yl, X₂) | —NMe₂ | 448 | 238, 278, 314 |
| 128 | (4,5,6,7-tetrahydro-3H-imidazo[4,5-c]pyridin-5-yl, X₁) | (1-methyl-2-phenylamino-1H-benzimidazol-5-yl, X₂) | —NMe₂ | 481 | 226, 266, 318 |
| 129 | (4,5,6,7-tetrahydro-3H-imidazo[4,5-c]pyridin-5-yl, X₁) | (1-(2-hydroxyethyl)-2-oxo-2,3-dihydro-1H-benzimidazol-5-yl, X₂) | —NMe₂ | 436 | 286 |

-continued
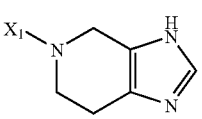
| # | R¹ | R² | R³ | MS (ESI) (M + H)⁺ | UV max [nm] |
|---|---|---|---|---|---|
| 130 |  | 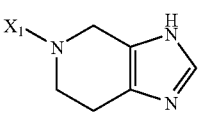 | —NMe₂ | 397 | 274, 318 |
| 131 | 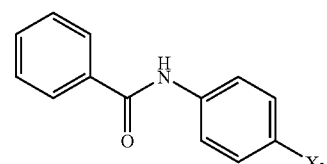 | 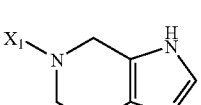 | —NMe₂ | 455 | 222, 262, 314 |
| 132 | 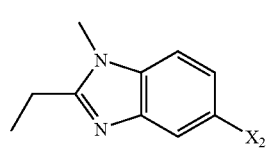 | 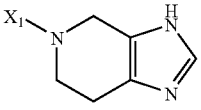 | —NMe₂ | 418 | 238, 282 |
| 133 | 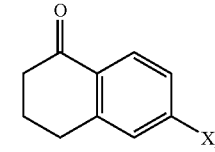 | 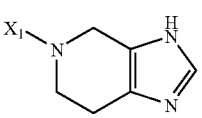 | —NMe₂ | 404 | 346 |
| 134 | 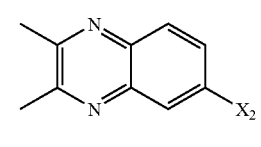 | 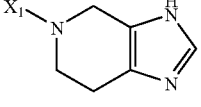 | —NMe₂ | 416 | 282 |
| 135 | 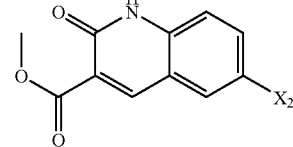 | 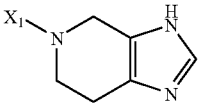 | —NMe₂ | 461 | 294 |
| 136 | 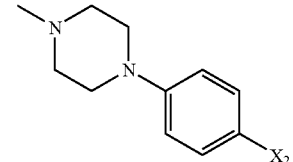 | 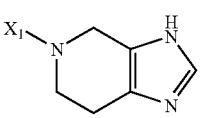 | —NMe₂ | 434 | 290 |
| 137 | 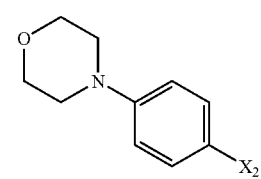 | | —NMe₂ | 421 | 290 |

-continued
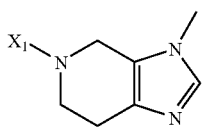
| # | R¹ | R² | R³ | MS (ESI) (M + H)⁺ | UV max [nm] |
|---|---|---|---|---|---|
| 138 | 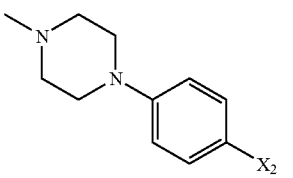 | 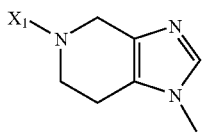 | —NMe₂ | 448 | 290 |
| 139 | 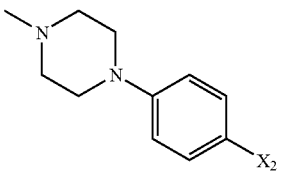 | 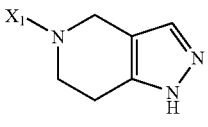 | —NMe₂ | 448 | 290 |
| 140 | 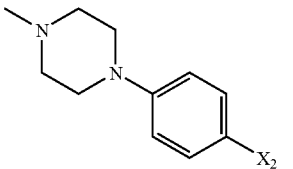 | 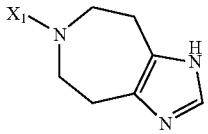 | —NMe₂ | 434 | 290 |
| 141 | 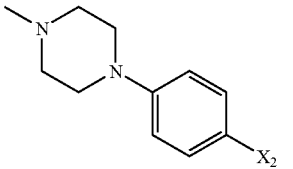 | 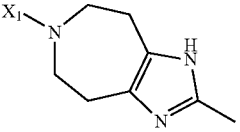 | —NMe₂ | 448 | 286 |
| 142 | 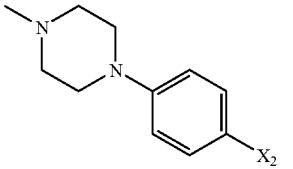 | 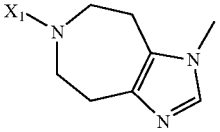 | —NMe₂ | 462 | 286 |
| 143 | 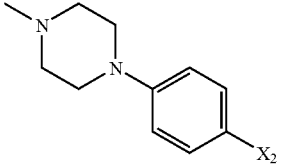 | 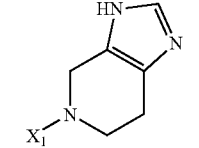 | —NMe₂ | 462 | 286 |
| 144 | 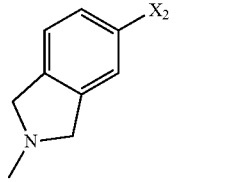 |  | —NMe₂ | 391 | 282 |

-continued

| # | R¹ | R² | R³ | MS (ESI) (M + H)⁺ | UV max [nm] |
|---|---|---|---|---|---|
| 145 | imidazo-tetrahydropyridine with X₁ | 4-(trifluoromethylsulfonyl)phenyl-X₂ | —NMe₂ | 468 | 330 |
| 146 | imidazo-tetrahydropyridine with X₁ | 4-methoxyphenyl-X₂ | —NMe₂ | 366 | 282 |
| 147 | imidazo-tetrahydropyridine with X₁ | 4-(trifluoromethyl)phenyl-X₂ | —NMe₂ | 404 | 298, 262 |
| 148 | imidazo-tetrahydropyridine with X₁ | 4-(methylsulfonyl)phenyl-X₂ | —NMe₂ | 414 | 310 |
| 149 | imidazo-tetrahydropyridine with X₁ | isobenzofuran-1(3H)-one-6-yl-X₂ | —NMe₂ | 392 | 230, 290 |
| 150 | imidazo-tetrahydropyridine with X₁ | isobenzofuran-1(3H)-one-5-yl-X₂ | —NMe₂ | 392 | 326 |
| 151 | imidazo-tetrahydropyridine with X₁ | 3-((dimethylamino)methyl)phenyl-X₂ | —NMe₂ | 393 | 286 |
| 152 | imidazo-tetrahydropyridine with X₁ | 4-(methylsulfonamido)phenyl-X₂ | —NMe₂ | 429 | 290 |

-continued
| # | R¹ | R² | R³ | MS (ESI) (M + H)⁺ | UV max [nm] |
|---|---|---|---|---|---|
| 153 | | | —NMe₂ | 433 | 290 |
| 154 | | | —NMe₂ | 442 | 322 |
| 155 | | | —NMe₂ | 414 | 290 |
| 156 | | | —NMe₂ | 366 | 294 |
| 157 | | | —NMe₂ | 404 | 286 |
| 158 | | | —NMe₂ | 378 | 242, 282 |
| 159 | | | —NMe₂ | 378 | 338 |
| 160 | | | —NMe₂ | 448 | 274 |

-continued

| # | R¹ | R² | R³ | MS (ESI) (M + H)⁺ | UV max [nm] |
|---|---|---|---|---|---|
| 161 | (imidazole-fused piperidine with ethyl, N-X₁) | 4-methylpiperazinyl-phenyl-X₂ | —NMe₂ | 462 | 278 |
| 162 | (imidazole-fused piperidine, N-X₁) | 4-methylpiperazinyl-(2-F)phenyl-X₂ | —NMe₂ | 452 | 290 |
| 163 | (imidazole-fused piperidine, N-X₁) | 4-methylpiperazinyl-(2-Cl)phenyl-X₂ | —NMe₂ | 468 | 290 |
| 164 | (imidazole-fused piperidine with methyl, N-X₁) | 4-methylpiperazinyl-phenyl-X₂ | —NMe₂ | 448 | 290 |
| 165 | (imidazole-fused piperidine, N-X₁) | 4-methylpiperazinyl-phenyl-X₂ | —NEtMe | 448 | 290 |
| 166 | (imidazole-fused piperidine, N-X₁) | 2-ethyl-benzimidazolyl-X₂ | —OMe | 391 | 242, 274, 306 |
| 167 | (imidazole-fused azepane, N-X₁) | piperidinyl-CH₂-phenyl-X₂ | —OMe | 434 | 278 |
| 168 | (imidazole-fused piperidine, N-X₁) | 4-ethylpiperazinyl-phenyl-X₂ | —OMe | 435 | 282 |

-continued

| # | R¹ | R² | R³ | MS (ESI) (M + H)⁺ | UV max [nm] |
|---|---|---|---|---|---|
| 169 | X₁–[imidazo-tetrahydropyridine] | Me-N-piperazine-phenyl-X₂ | —OMe | 421 | 282 |
| 170 | X₁–[imidazo-tetrahydroazepine] | Me-N-piperazine-phenyl-X₂ | —OMe | 435 | 282 |
| 171 | X₁–[2-methyl-imidazo-tetrahydroazepine] | Me-N-piperazine-phenyl-X₂ | —OMe | 449 | 282 |
| 172 | X₁–[2-amino-thiazolo-tetrahydroazepine] | Me-N-piperazine-phenyl-X₂ | —OMe | 467 | 278 |
| 173 | X₁–[N-methyl-imidazo-tetrahydroazepine] | Me-N-piperazine-phenyl-X₂ | —OMe | 449 | 282 |
| 174 | X₁–[2-methylthio-imidazo-tetrahydroazepine] | Me-N-piperazine-phenyl-X₂ | —OMe | 481 | 278 |
| 175 | X₁–[imidazo-tetrahydroazepine] | morpholine-phenyl-X₂ | —OMe | 422 | 282 |

-continued
| # | R¹ | R² | R³ | MS (ESI) (M + H)⁺ | UV max [nm] |
|---|---|---|---|---|---|
| 176 | 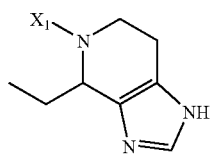 | 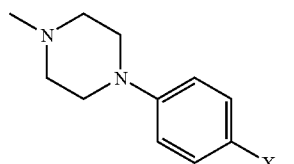 | —OMe | 449 | 274 |
| 177 | 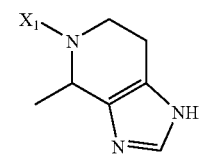 | 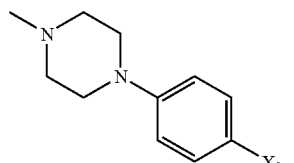 | —OMe | 435 | 274 |
| 178 | 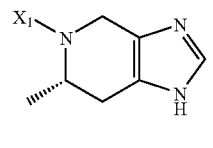 | 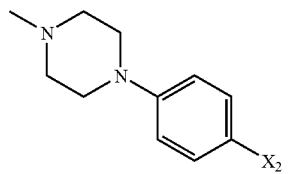 | —OMe | 435 | 282 |
| 179 | 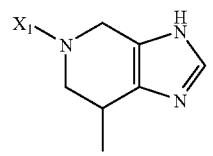 | 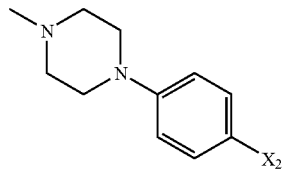 | —OMe | 435 | 282 |
| 180 | 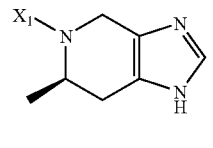 | 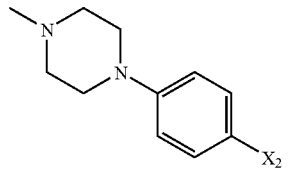 | —OMe | 435 | 282 |
| 181 | 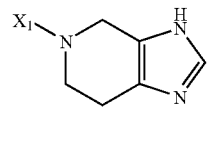 | 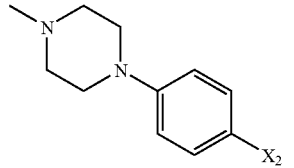 | 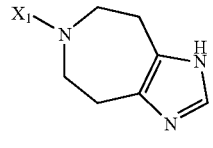 | 431 | 282 |
| 182 | 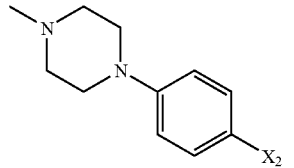 | | | 445 | 282 |

-continued

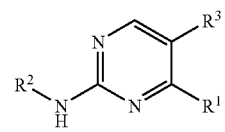

| # | R¹ | R² | R³ | MS (ESI) (M + H)⁺ | UV max [nm] |
|---|----|----|----|----|----|
| 183 | 4,5,6,7-tetrahydroimidazo[4,5-c]pyridin-5-yl (X₁) | 4-(4-methylpiperazin-1-yl)phenyl (X₂) | isopropyl (X₃) | 433 | 282 |
| 184 | 4,5,6,7-tetrahydroimidazo[4,5-c]pyridin-5-yl (X₁) | 4-(4-methylpiperazin-1-yl)phenyl (X₂) | N-ethyl-N-methylamino (X₃) | 448 | 290 |
| 185 | 4,5,6,7-tetrahydroimidazo[4,5-c]pyridin-5-yl (X₁) | 4-(4-methylpiperazin-1-yl)phenyl (X₂) | N-benzyl-N-methylamino (X₃) | 510 | 290 |
| 186 | 4,5,6,7-tetrahydroimidazo[4,5-c]pyridin-5-yl (X₁) | 4-(4-methylpiperazin-1-yl)phenyl (X₂) | methylamino (X₃) | 420 | 290 |
| 187 | 4,5,6,7-tetrahydroimidazo[4,5-c]pyridin-5-yl (X₁) | 6-(4-methylpiperazin-1-yl)pyridin-3-yl (X₂) | acetyl (X₃) | 433 | 334, 246 |
| 188 | 4,5,6,7-tetrahydroimidazo[4,5-c]pyridin-5-yl (X₁) | 4-morpholinophenyl (X₂) | propanoyl (X₃) | 420 | 334, 246 |
| 189 | 4,5,6,7-tetrahydroimidazo[4,5-c]pyridin-5-yl (X₁) | 4-(4-methylpiperazin-1-yl)phenyl (X₂) | acetyl (X₃) | 447 | 334, 246 |

-continued

| # | R¹ | R² | R³ | MS (ESI) (M + H)⁺ | UV max [nm] |
|---|---|---|---|---|---|
| 190 | X₁–[imidazo-tetrahydropyridinyl] | [piperidinyl-CH₂-C₆H₄-X₂] | X₃–ethyl | 418 | 278 |
| 191 | X₁–[imidazo-tetrahydropyridinyl] | [piperidinyl-CH₂-C₆H₄-X₂] | X₃–C(=O)– | 432 | 326 |

Example 192

2-[4-(2-pyrrolidin-1-yl-ethylcarbamoyl)-phenylamino]-4-(3,4,6,7-tetrahydro-imidazo[4,5-c]pyridin-5-yl)-5-dimethylamino-1-pyrimidine

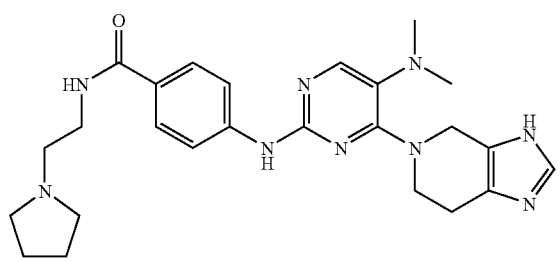

35 mg 2-(4-carboxy-phenylamino)-4-(3,4,6,7-tetrahydro-imidazo[4,5-c]pyridin-5-yl)-5-dimethylamino-pyrimidine (prepared analogously to Example 63) is dissolved in 0.2 mL DMF, and combined with 64 µL triethylamine, 33 mg O-(benzotriazol-1-yl)-N,N,N',N'-tetramethyluronium-tetrafluoroborate and 1-(2-aminoethyl)-pyrrolidine. After being stirred for 15 h at RT the reaction solution is purified by column chromatography. The carrier material used is C18-RP-silica gel and a gradient is run through which consists at the starting point of 80% water (10 mM ammonium hydrogen carbonate and 38 mM ammonia) and 20% acetonitrile and at the finishing point of 35% water and 65% acetonitrile. Fractions are freeze-dried. The residue is taken up in acetonitrile, combined with aqueous hydrochloric acid and freeze-dried again.

Yield: 40 mg
UV max: 315 nM
MS (ESI): 476 (M+H)⁺

Example 193-232

The following compounds are prepared by a process analogous to that described in Example 192. The acid component for Examples 228 to 232 may be obtained by saponification of the methyl ester (see Example 14).

| # | R² | MS (ESI) (M + H)⁺ | UV max [nm] |
|---|---|---|---|
| 193 | X₂–C₆H₄–C(=O)–NH–CH₂CH₂CH₃ | 421 | 314 |

-continued
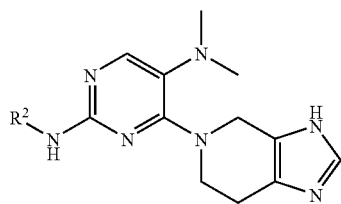
| # | R² | MS (ESI) (M + H)⁺ | UV max [nm] |
|---|---|---|---|
| 194 | X₂-C₆H₄-C(O)-N(4-methylpiperazin-1-yl) | 462 | 306 |
| 195 | X₂-C₆H₄-C(O)-NH-CH₂-C(O)-N(CH₃)₂ | 478 | 306 |
| 196 | X₂-C₆H₄-C(O)-NH-CH₂-cyclopropyl | 433 | 314 |
| 197 | X₂-C₆H₄-C(O)-NH-CH₂CH₂-F | 425 | 314 |
| 198 | X₂-C₆H₄-C(O)-NH-CH₂CH₂-OCH₃ | 435 | 314 |
| 199 | X₂-C₆H₄-C(O)-N(CH₃)₂ | 437 | 314 |
| 200 | X₂-C₆H₄-C(O)-morpholin-4-yl | 407 | 302 |
| 201 | X₂-C₆H₄-C(O)-NH-n-butyl | 449 | 306 |

-continued
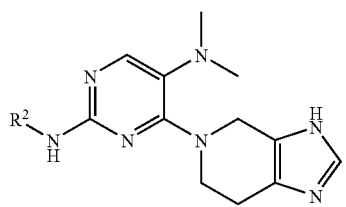
| # | R² | MS (ESI) (M + H)⁺ | UV max [nm] |
|---|---|---|---|
| 202 | ![X₂-C6H4-C(O)-NH-C6H4-N(CH3)2] | 498 | 322 |
| 203 | ![X₂-C6H4-C(O)-NH-benzimidazole] | 495 | 334-342 |
| 204 | ![X₂-C6H4-C(O)-NH-(N-methyl)benzimidazole] | 509 | 322 |
| 205 | ![X₂-C6H4-C(O)-NH-C6H4-(N-methylpiperazine)] | 553 | 322-326 |
| 206 | ![X₂-C6H4-C(O)-NH-phenyl] | 455 | 302 |
| 207 | ![X₂-C6H4-C(O)-N(Me)-phenyl] | 469 | 222-226 |
| 208 | ![X₂-C6H4-C(O)-NH-cyclohexyl-morpholine] | 546 | 294 |
| 209 | ![X₂-C6H4-C(O)-NH-cyclobutyl-morpholine] | 518 | 294-298 |

-continued
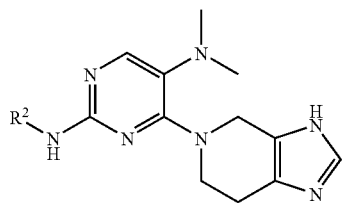
| # | R² | MS (ESI) (M + H)⁺ | UV max [nm] |
|---|---|---|---|
| 210 | X₂-C₆H₄-C(O)-N(piperazine)N-(4-pyridyl) | 525 | 262; 302-306 |
| 211 | X₂-C₆H₄-C(O)-N(piperazine)N-phenyl | 524 | 242-246; 302-306 |
| 212 | phenyl-C(O)-N(piperazine)N-CH₂-phenyl | 538 | 302-306 |
| 213 | X₂-C₆H₄-C(O)-N(piperazine)N-(4-CF₃-phenyl) | 592 | 262-270; 298-306 |
| 214 | X₂-C₆H₄-C(O)-N(piperazine)N-CH₂CH₂-OCH₃ | 506 | 302-310 |
| 215 | X₂-C₆H₄-C(O)-N(piperazine)N-iPr | 490 | 302-310 |
| 216 | X₂-C₆H₄-C(O)-N(piperazine)N-C(O)CH₃ | 490 | 306-310 |

-continued
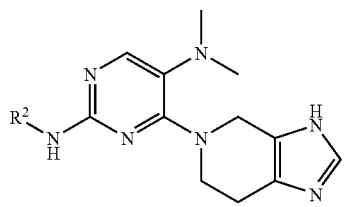
| # | R² | MS (ESI) (M + H)⁺ | UV max [nm] |
|---|---|---|---|
| 217 | ![structure: X₂-C₆H₄-C(O)-piperazine-pyrazine] | 526 | 250-254; 306-310 |
| 218 | ![structure: X₂-C₆H₄-C(O)-piperazine-(2,4-difluorophenyl)] | 560 | 302-306 |
| 219 | ![structure: X₂-C₆H₄-C(O)-piperazine-CH₂CH₂-4-pyridyl] | 553 | 302-310 |
| 220 | ![structure: X₂-C₆H₄-C(O)-piperazine-2-pyridyl] | 525 | 246-250; 302-310 |
| 221 | ![structure: X₂-C₆H₄-C(O)-N-methyl-diazabicyclic] | 474 | 306-310 |

-continued
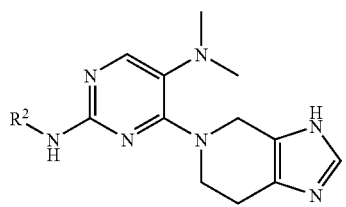
| # | R² | MS (ESI) (M + H)⁺ | UV max [nm] |
|---|---|---|---|
| 222 | 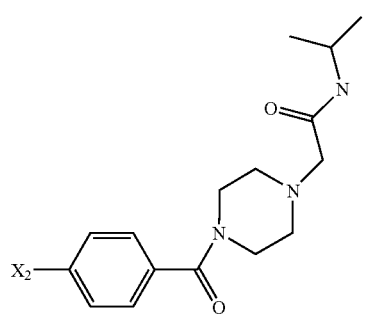 | 547 | 302-310 |
| 223 | 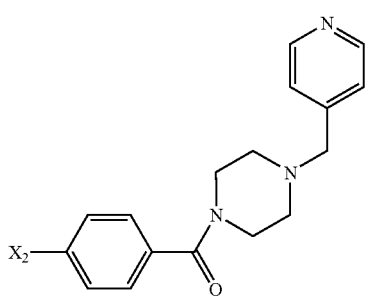 | 539 | 302-310 |
| 224 | 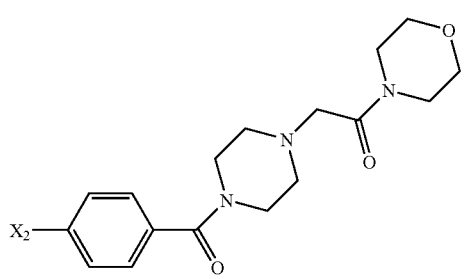 | 575 | 302-310 |
| 225 | 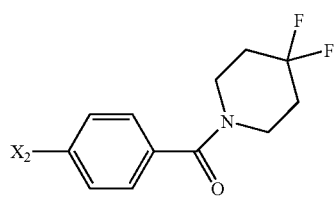 | 483 | 306 |
| 226 | 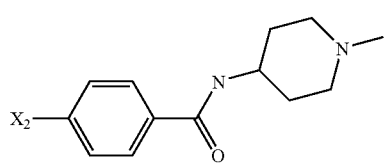 | 476 | 314 |

-continued
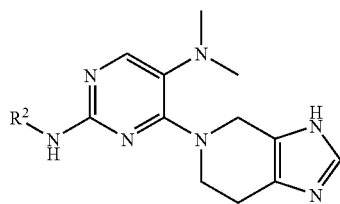
| # | R² | MS (ESI) (M + H)⁺ | UV max [nm] |
|---|---|---|---|
| 227 | (1-methylpiperidin-4-yl)(N-methyl)-NHC(O)-C₆H₄-X₂ | 490 | 302 |
| 228 | pyrrolidin-1-yl-ethyl-NHC(O)-C₆H₄-X₂ | 476 | 315 |
| 229 | X₂-C₆H₄-N(piperidine)-C(O)-N(4,4-difluoropiperidine) | 566 | 290 |
| 230 | X₂-C₆H₄-N(piperidine)-C(O)-N(3,3-difluoropiperidine) | 566 | 286 |
| 231 | X₂-C₆H₄-N(piperidine)-C(O)-morpholine | 532 | 290 |
| 232 | X₂-C₆H₄-N(piperidine)-C(O)-N(2,6-dimethylmorpholine) | 560 | 290 |

Example 233

2-(3-(4-cyanomethyl-piperazin-1-yl)-phenylamino)-4-(3,4,6,7-tetrahydro-imidazo[4,5-c]pyridin-5-yl)-5-dimethylamino-1-pyrimidine

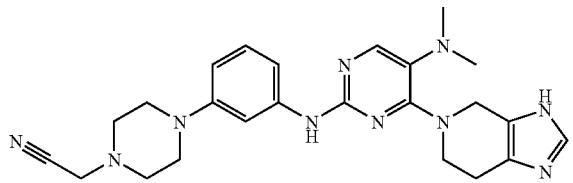

45 mg 2-(3-piperazin-1-yl-phenylamino)-4-(3,4,6,7-tetrahydro-imidazo[4,5-c]pyridin-5-yl)-5-methoxy-pyrimidine (prepared analogously to Example 1) is dissolved in 0.5 mL DMA and combined with 6.8 μL chloroacetonitrile and 15.2 mg potassium carbonate 33 mg. After being stirred for 15 h at RT the reaction solution is purified by column chromatography. The carrier material used is C18-RP-silica gel and a gradient is run through which consists at the starting point of 80% water (10 mM ammonium hydrogen carbonate and 20 mM ammonia) and 20% acetonitrile and at the finishing point of 35% water and 65% acetonitrile. The appropriate fractions are freeze-dried. The residue is taken up in acetonitrile, combined with aqueous hydrochloric acid and freeze-dried once again.

Yield: 17.5 mg
UV max: 244 nM
MS (ESI): 459 (M+H)+

Examples 234-236

The following compounds are prepared by a process analogous to that described in Example 233. The corresponding amines are described in the literature or are commercially obtainable.

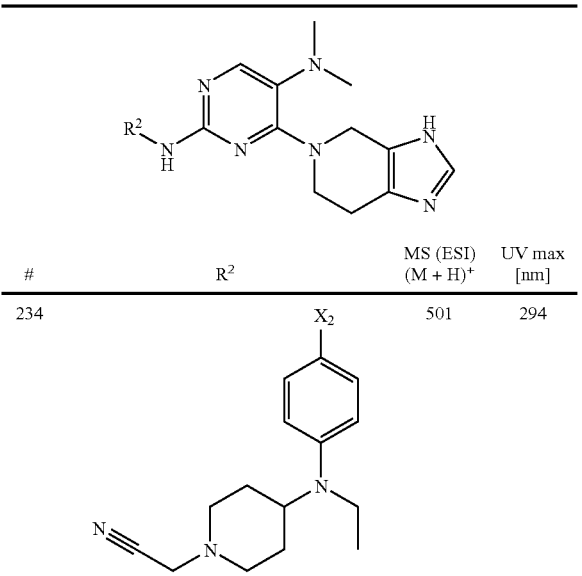

| # | R² | MS (ESI) (M + H)+ | UV max [nm] |
|---|---|---|---|
| 234 | (4-X₂-phenyl-N(Et)-piperidin-4-yl-N-CH₂CN) | 501 | 294 |

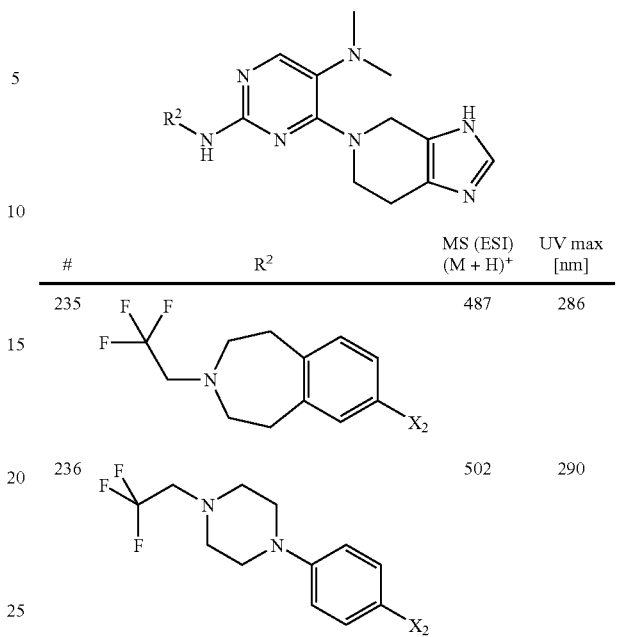

| # | R² | MS (ESI) (M + H)+ | UV max [nm] |
|---|---|---|---|
| 235 | (CF₃CH₂-N-benzazepine-X₂) | 487 | 286 |
| 236 | (CF₃CH₂-piperazine-phenyl-X₂) | 502 | 290 |

Example 237

2-[4-(furan-3-yl)-phenylamino]-4-(3,4,6,7-tetrahydro-imidazo[4,5-c]pyridin-5-yl)-5-dimethylamino-1-pyrimidine

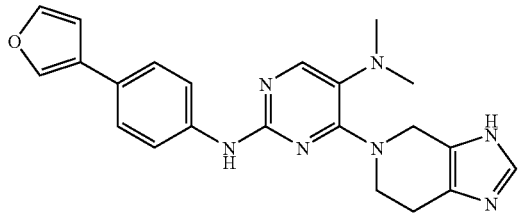

a) 4-furan-3-yl-1-nitrobenzene 200 mg 4-bromonitrobenzene, 110.8 mg furan-3-boric acid and 162 mg palladium/C are dissolved in 3 mL 1,4-dioxane. Then 965.3 mg caesium carbonate (dissolved in 586 μL water) are added. The reaction is completed in the microwave (110° C.) after 100 min. After aqueous working up the mixture is extracted with ethyl acetate and died on magnesium sulphate. The solvent is eliminated in vacuo. This crude product is used in the following reaction without further purification.

b) 4-furan-3-yl-phenylamine 277 mg 4-furan-3-yl-1-nitrobenzene are dissolved in 40 ml of methanol and combined with 200 mg palladium/C. The suspension is shaken at 25° C. for 60 h under a H₂ pressure of 5 bar. Then the solvent is eliminated in vacuo. The crude mixture is purified by column chromatography. The carrier material used is silica gel and the mobile phase used is a solvent mixture of cyclohexane/ethyl acetate 50/50. The suitable fractions are freed from the solvent in vacuo.

Yield: 82 mg
MS (ESI): 160 (M+H)$^+$ c) 2-[4-(furan-3-yl)-phenylamino]-4-(3,4,6,7-tetrahydro-imidazo[4,5-c]pyridin-5-yl)-5-dimethylamino-pyrimidine This compound is prepared analogously to Example 63 using 4-furan-3-yl-phenylamine instead of 4-dimethylaminomethyl-phenylamine.

Yield: 40 mg
UV max: 302 nM
MS (ESI): 402 (M+H)$^+$

Example 238-243

The following compounds are prepared by a process analogous to that described in Example 237. The corresponding amines are described in the literature or are commercially obtainable.

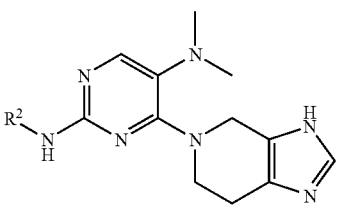

| # | R$^2$ | MS (ESI) (M + H)$^+$ | UV max [nm] |
|---|---|---|---|
| 238 | 4-pyridyl-phenyl | 413 | 330 |
| 239 | 3-pyridyl-phenyl | 413 | 317 |
| 240 | pyrimidinyl-phenyl | 414 | 325 |
| 241 | 2-pyridyl-phenyl | 413 | 326 |
| 242 | pyrrol-3-yl-phenyl | 401 | 305 |
| 243 | pyrrol-2-yl-phenyl | 401 | 318 |

The following Examples describe the biological activity of the compounds according to the invention without restricting the invention to these Examples.

The effect of the compounds according to the invention on various kinases, for example on serine-threonine kinase PDK1, is determined in in vitro kinase assays with recombinantly prepared protein. The compounds in this assay exhibit good to very good activity, i.e. for example an IC$_{50}$ value of less than 1 μmol/L, generally less than 0.1 μmol/L.

Example PDK1 Kinase Assay

Recombinant human PDK1 enzyme (aa 52-556) attached to His$_6$ at its N-terminal end is isolated from Baculovirus-infected insect cells. Purified enzyme may also be obtained for example through Upstate.

The following components are combined in a well of a 96-well round-bottomed plate (Greiner bio-one, No. 650101):

7.5 μL of the compound to be tested in a variable concentration (e.g. beginning at 10 μM, and dilution in 1:5) in 3.33% DMSO (1% DMSO final concentration)/assay buffer (50 mM Tris pH 7.5, 0.05% β-mercaptoethanol, 10 mM magnesium acetate)

7.5 μL PDK1 (10 ng/well) and PDKtide (KTFCGTPEY-LAPEVRREPRILSEEEQEMFRDFDYIADWC) synthesised by Pepceuticals Limited, Nottingham, United Kingdom; 25 μM final concentration; PDK1 and PDKtide are correspondingly diluted together in assay buffer; PDKtide is present in this mixture as an 83.3 μM solution)

10 μL ATP solution (25 μM ATP with 0.5 μCi/well of gamma-P33-ATP)

The reaction is started by adding the ATP solution and incubated for 30 min at RT; at the start of the reaction the plates are shaken gently. The reaction is stopped by the addition of 5 μL/well 0.5 M phosphoric acid (H$_3$PO$_4$) and incubated for about 20 min at RT. The precipitate is transferred by harvesting onto filter plates (96-well microtitre filter plate: UniFilter GF/C; Perkin Elmer; No. 6005174), then washed 6 times with 50 mM $H_3PO_4$ and dried at 60° C. Then the plate is stuck down with sealing tape, 25 µL/well of scintillation solution (Microscint 0; Perkin Elmer; No. 6013611) are added and the amount of P33 precipitated is measured using the Wallac Betacounter. The measurement data are evaluated using the Standard Graphpad software.

The antiproliferative activity of the compounds according to the invention is determined on cultivated human tumour cells, for example on PC-3 cells. The compounds exhibit good to very good activity, i.e. for example an $EC_{50}$ value of less than 5 µmol L, generally less than 1 µmol L in the PC-3 proliferation test.

Measurement of the Inhibition of Proliferation on Cultivated Human Tumour Cells

To measure proliferation on cultivated human tumour cells, cells of prostate carcinoma tumour cell line PC-3 (obtained from American Type Culture Collection (ATCC)) are cultivated in Ham's F12 Medium (Gibco) and 10% foetal calf serum (Gibco) and harvested in the log growth phase. Then the PC-3 cells are placed in 96-well plates (Costar) at a density of 1000 cells per well and incubated overnight in an incubator (at 37° C. and 5% CO2), while on each plate 16 wells are used as controls (8 wells with cells to which only DMSO solution has been added (should yield 30-50% maximum value of reduced AlamarBlue), 4 wells containing only medium (medium control, after the addition of oxidised AlamarBlue reagent the background signal is obtained) and 4 wells where again only medium is added (after the addition of reduced AlamarBlue reagent it acts as a maximum value)). The active substances are added to the cells in various concentrations (dissolved in DMSO; DMSO final concentration: 0.1% or 1%) (in each case as a double or triple measurement). After 5 days' incubation 20 µl AlamarBlue reagent (Serotec) are added to each well, and the cells are incubated for a further 5-7 hours. As a control, 20 µl reduced AlamarBlue reagent is added to each of 4 wells. After incubation the colour change of the AlamarBlue reagent in the individual wells is determined in a SpectraMax Photometer (Molecular Devices) (extinction 530 nm, emission 590 nm, 5 sec measuring time). The amount of AlamarBlue reagent reacted represents the metabolic activity of the cells. The relative cell activity is calculated in relation to the control (PC-3 cells without inhibitor) and the active substance concentration which inhibits the cell activity by 50% (EC50) is derived. The values are calculated from the average of two or three individual measurements.

The compounds according to the invention are also tested accordingly on other tumour cells. For example these compounds are effective on carcinomas of all kinds of tissue (e.g. gliomas (U87), sarcoma (e.g. MES-SA, SK-UT-1B), breast (MDA-MB468), colon (HCT 116), lung (H460)) and could be used in indications of this kind, particularly in indications which have activating changes in the PI3K-AKT-PDK1 signal pathway. This demonstrates the wide range of applications for the compounds according to the invention for the treatment of all kinds of tumour types.

On the basis of their biological properties the new compounds of general formula (1) or (1A), the isomers and the physiologically acceptable salts thereof are therefore suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, giant cell tumour, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma; vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) or (1A) may be used on their own or in combination with other active substances according to the invention, optionally also in combination with other pharmacologically active substances.

Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples that follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the formula (1A),

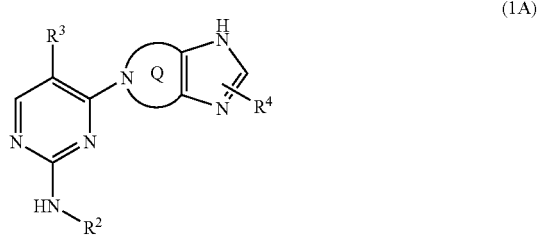

(1A)

wherein

Q denotes 5, 6 or 7 membered heterocycloalkyl;

$R^2$ denotes 9 membered heteroaryl, substituted by one or more identical or different $R^4$, or $R^2$ denotes 9 membered heterocycloalkyl substituted by one or more identical or different $R^4$, or $R^2$ denotes phenyl substituted by a 5-6 membered heterocycloalkyl, which may optionally be substituted by one or more identical or different $R^c$ and/or $R^b$, or $R^2$ denotes phenyl substituted by —$NR^cR^c$, —$C(O)R^c$ or —$C(O)NR^cR^c$, and $R^3$ denotes dimethylamino or methoxy, and $R^4$ denotes a group selected from among $R^a$, $R^b$ and $R^a$ substituted by one or more identical or different $R^c$ and/or $R^b$;

each $R^a$ is selected independently of one another from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^b$ is a suitable group and each is independently selected from among =O, —$OR^c$, $C_{1-3}$haloalkyloxy, —$OCF_3$, =S, —$SR^c$, =$NR^c$, $NOR^c$, —$NR^cR^c$, halogen, —$CF_3$, —CN, —NC, —OCN, —SCN, —$NO_2$, —$S(O)R^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)_2NR^cR^c$, —$C(O)R^c$, —$C(O)OR^c$, —$C(O)NR^cR^c$, —$CN(R^f)NR^cR^c$, —$CN(OH)R^c$, —$CN(OH)NR^cR^c$, —$OC(O)R^c$, —$OC(O)OR^c$, —$OC(O)NR^cR^c$, —$OCN(R^f)NR^cR^c$, —$N(R^f)C(O)R^c$, —$N(R^f)C(S)R^c$, —$N(R^f)S(O)_2R^c$, —$N(R^f)C(O)OR^c$, —$N(R^f)C(O)$ $NR^cR^c$, —$[N(R^f)C(O)]_2R^c$, —$N[C(O)]_2R^c$, —$N[C(O)]_2$ $OR^c$, —$[N(R^f)C(O)]_2OR^c$ and —$N(R^f)CN(R^f)NR^cR^c$;

each $R^c$ independently of one another denotes hydrogen or a group optionally substituted by one or more identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^d$ independently of one another denotes hydrogen or a group optionally substituted by one or more identical or different $R^e$ and/or $R^f$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^e$ is a suitable group and each is independently selected from among =O, —$OR^f$, $C_{1-3}$haloalkyloxy, —$OCF_3$, =S, —$SR^f$, =$NR^f$, =$NOR^f$, —$NR^fR^f$, halogen, —$CF_3$, —CN, —NC, —OCN, —SCN, —$NO_2$, —$S(O)R^f$, —$S(O)_2R^f$, —$S(O)_2OR^f$, —$S(O)NR^fR^f$, —$S(O)_2NR^fR^f$, —$OS(O)R^f$, —$OS(O)_2R^f$, —$OS(O)_2OR^f$, —$OS(O)_2NR^fR^f$, —$C(O)R^f$, —$C(O)OR^f$, —$C(O)NR^fR^f$, —$CN(R^g)NR^fR^f$, —$CN(OH)R^f$, —$C(NOH)NR^fR^f$, —$OC(O)R^f$, —$OC(O)OR^f$, —$OC(O)NR^fR^f$, —$OCN(R^g)NR^fR^f$, —$N(R^g)C(O)R^f$, —$N(R^g)C(S)R^f$, —$N(R^g)S(O)_2R^f$, —$N(R^d)C(O)OR^f$, —$N(R^g)C(O)NR^fR^f$, and —$N(R^g)CN(R^f)NR^fR^f$;

each $R^f$ independently of one another denotes hydrogen or a group optionally substituted by one or more identical or different $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, or a tautomer, racemate, enantiomer, diastereomer or mixture thereof or pharmacologically acceptable salt thereof.

2. A pharmaceutical composition comprising a compound of the formula (1A) according to claim 1, or a pharmaceutically effective salts thereof, and an exipient or carrier.

3. A method for the treatment of breast cancer which comprises administering to a host suffering from breast cancer a therapeutically effective amount of a compound according to claim 1.

* * * * *